(12) United States Patent
Yurugi et al.

(10) Patent No.: US 7,321,051 B2
(45) Date of Patent: Jan. 22, 2008

(54) COMPOSITION OF VINYL ETHER GROUP-CONTAINING (METH) ACRYLIC ESTER AND PRODUCTION METHOD THEREOF

(75) Inventors: Keiji Yurugi, Osaka (JP); Hiroko Yamaguchi, Osaka (JP)

(73) Assignee: Nippon Shokubai Co., Ltd., Osaka (JP)

( * ) Notice: Subject to any disclaimer, the term of this patent is extended or adjusted under 35 U.S.C. 154(b) by 290 days.

(21) Appl. No.: 09/982,861

(22) Filed: Oct. 22, 2001

(65) Prior Publication Data

US 2002/0143120 A1 Oct. 3, 2002

(30) Foreign Application Priority Data

Oct. 23, 2000 (JP) ............................. 2000-322575

(51) Int. Cl.
C07C 69/52 (2006.01)
(52) U.S. Cl. ....................................... 560/205; 560/220
(58) Field of Classification Search ................ 560/201, 560/217, 205, 207, 211, 218
See application file for complete search history.

(56) References Cited

U.S. PATENT DOCUMENTS

| | | | | |
|---|---|---|---|---|
| 2,692,256 A * | 10/1954 | Bauer et al. | ................. | 526/320 |
| 5,264,307 A | 11/1993 | Andrei et al. | | |
| 5,968,322 A | 10/1999 | Arnoldy et al. | | |
| 6,384,146 B1 * | 5/2002 | Ruckenstein et al. | ........ | 525/242 |

FOREIGN PATENT DOCUMENTS

| | | | |
|---|---|---|---|
| CA | 2221543 | | 6/1998 |
| DE | 1027401 | | 4/1958 |
| DE | 1034363 | | 7/1958 |
| EP | 2000-154223 | | 6/2000 |
| GB | 976304 | * | 3/1961 |
| GB | 976304 A | | 11/1964 |
| JP | 34-2689 | | 6/1931 |
| JP | 40-27056 | | 11/1940 |
| JP | 47-31922 | | 11/1972 |
| JP | 48-34112 | | 5/1973 |
| JP | 48-75637 | | 10/1973 |
| JP | 49-125315 | | 11/1974 |
| JP | 55-39533 | | 10/1980 |
| JP | 61-275231 | | 5/1986 |
| JP | 05-286895 | | 2/1993 |
| JP | 10-183025 | | 7/1998 |
| WO | WO 00/59968 A1 | | 10/2000 |

OTHER PUBLICATIONS

Vansteenkiste et al. Prepration of Tailor-Made Multifunctional Propenyl Ethers by Radical Copolymerization of 2-(1-Propenyl)oxyethyl Methacrylate, Macromolecules 1999, 32, 55-59.*

Kirk-Othmer Encyclopedia of Chemical Technology, Acrylic Acid and Derivatives.*

Trofimov et al., Zhurnal Organicheskoi Khimii (1982), 18(3), 528-31.*

Kartashova et al., Osn. Organ. Sintez i Neftekhimiya, Yaroslavl (1989), (25), 42-6.*

Journal of Polymer Science, Part A: Polymer Chemistry, vol. 30, 2365-2369 (1992) "Photocrosslinking of Copolymers of Vinyloxyethyl Methacrylate-Styrene Initiated by Sulfonium Salts. I. Transient Species Formed on Photolysis of Sulfonium Salt".

Journal of Polymer Science, Part A: Polymer Chemistry, vol. 36, 1865-1872 (1998) "A Novel Route to Poly(2-hydroxyethyl methacrylate and Its Amphiphilic Block Copolymers".

Journal of Polymer Science, vol. XLIV, pp. 523-529 (1960) "Effect of Type of Catalyst on Structure of Poly($\beta$-Vinyloxyethyl Methacrylate)".

Journal of Applied Polymer Science, vol. 20, 1122-1124 (1976) Notes "Investigation of photopolymers. XII. Synthesis of photopolymers by cationic polymerization of Vinyloxyethly acrylate and Vinyloxyethyl solvent in some acryl esters".

Journal of Polymer Science, vol. 21, No. 8, pp. 649-653 (1989) "Synthesis of Some Tailor-Made Poly(benzo-19-crown-6)s via cyclopolymerization of Divinyl Ether with Hydrogen Iodide/Iodine Initiator".

Journal of Organic Chemistry of the USSR, pp. 462-465 "Synthesis of vinyl ethers and sulfides with methacrylate groups".

Journal of Applied Chemistry of the USSR, pp. 1017-1022 (1985) "Vinyloxyethyl esters of monocarboxylic acids".

(Continued)

*Primary Examiner*—Karl Puttlitz
(74) *Attorney, Agent, or Firm*—Sughrue Mion, PLLC

(57) ABSTRACT

It is an object of the present invention to provide a vinyl ether group-containing (meth)acrylic ester, which has both radical polymerizability and cation polymerizability, improved in storage stability and stability in handling without impairing its polymerizability or, in other words, provide a stabilized vinyl ether group-containing (meth)acrylic ester. Another object is to provide a method of producing a stabilized vinyl ether group-containing (meth)acrylic ester composition. A further object is to provide a method of stably handing, a method of economically and stably producing and a method of purifying a vinyl ether group-containing (meth)acrylic ester.

A vinyl ether group-containing (meth)acrylic ester composition which comprises a radical polymerization inhibitor and a vinyl ether group-containing (meth)acrylic ester represented by the following general formula (1):

$$CH_2=CR_1-COO-R_2-O-CH=CH-R_3 \quad (1)$$

in the formula, R1 represents a hydrogen atom or a methyl group, R2 represents an organic residue and R3 represents a hydrogen atom or an organic residue.

3 Claims, No Drawings

OTHER PUBLICATIONS

Macromolecules, vol. 31, No. 3, 1998, pp. 746-752 "Graft Copolymers by Combined Anionic and Cationic Polymerizations Based on the Homopolymerization of a Bifunctional Monomer".

Makromolekulare Chemie 175, 3357-3366 (1974), Study of Photopolymer, 10.

Farbe & Lack, Pigments and Paints 103, vol. 2/97, pp. 58-62 "Reactive Microgels Containing Vinyl Ether Groups".

β-Vinyloxyethyl Methacrylate, pp. 421-424.

УпК 547.391.3'421.4, pp. 42-46 "Synthesis of Vinyloxyethyl methacrylate in the presence of tetra-butoxy titanium".

Nipponkagakukaishi, No. 8, pp. 1581-1583 (1974).

Aldrich: "Katalog Handbuch Feinchemikalien 1996-1997", 1996, pp. 31-34.

Aldrich: "Katalog Handbuch Feinchemikalien 1996-1997", 1996, pp. 325, 777, 1421.

"*Methacrylic Acid and Derivatives*" in Kirk-Othmer Encyclopedia of Chemical Technology, Copyright © 1995, by John Wiley & Sons, Inc., vol. 16, pp. 227-270.

"*Methacrylic Acid and Derivatives*", by W. Bauer, Jr., in Ullman's Encyclopedia of Industrial Chemistry, Copyright © 2002, by Wiley-VCH Verlag GmbH & Co., KGaA, Article Online Posting Date, Jun. 15, 2000, pp. 1-13.

\* cited by examiner

COMPOSITION OF VINYL ETHER GROUP-CONTAINING (METH) ACRYLIC ESTER AND PRODUCTION METHOD THEREOF

TECHNICAL FIELD

The present invention relates to a vinyl ether group-containing (meth)acrylic ester composition and a method of producing the same as well as to a method of handling, a method of producing and a method of purifying a vinyl ether group-containing (meth)acrylic ester.

More particularly, it relates to a composition comprising a vinyl ether group-containing (meth)acrylic ester having different kinds of polymerizable groups within the molecule and capable of being easily homopolymerized or copolymerized with some other polymerizable compounds by means of heat, ultraviolet rays, radiant rays, electron beams, radical polymerization initiators or acids, etc., and a method of producing the same as well as to a method of handling, a method of producing and a method of purifying said vinyl ether group-containing (meth)acrylic ester.

BACKGROUND ART

Vinyl ether group-containing (meth)acrylic esters have different kinds of polymerizable groups, namely radical- and anion-polymerizable (meth)acryloyl groups and cation-polymerizable vinyl ether groups, within molecules and, therefore, they are useful compounds which can be used in a wide range of industrial use as raw materials in medicinal chemicals and agrochemicals, as synthetic intermediates and further as polymerizable materials.

A number of studies have been made on the radical polymerizability and cation polymerizability of vinyl ether group-containing (meth)acrylic esters. However, because of their easy radical polymerizability and cation polymerizability, vinyl ether group-containing (meth)acrylic esters are poor in stability, which leads to impurity formation, peroxide formation and polymerization during storage or handling thereof, hence they can hardly be said to be put into fully practical use.

For methods of producing vinyl ether group-containing (meth)acrylic esters, there are known the method comprising subjecting (meth)acrylic acids and hydroxyl group-containing vinyl ethers to esterification (method A), the method comprising subjecting (meth)acrylic halides and hydroxyl group-containing vinyl ethers to esterification (method B), the method comprising subjecting (meth)acrylic anhydrides and hydroxyl group-containing vinyl ethers to esterification (method C), and the method comprising subjecting (meth) acrylic esters and hydroxyl group-containing vinyl ethers to transesterification (method D), and the like. The above esters can also be produced by the method comprising subjecting (meth)acrylic acids and halogen-containing vinyl ethers to esterification (method E) and by the method comprising subjecting (meth)acrylic acid alkali (or alkaline earth) metal salts and halogen-containing vinyl ethers to esterification (method F).

Of these production methods, those methods using halogen-containing vinyl ethers as starting materials cause the formation of an equimolar amount of by product salts. Therefore, those production methods using hydroxyl group-containing vinyl ethers as starting materials are suitable from the industrial viewpoint. Since, however, hydroxyl group-containing vinyl ethers are generally produced by the addition reaction of diol to acetylene (the so-called Reppe reaction) or by the gaseous phase dehydration reaction of diol-monoalkylene oxide adduct, a number of impurities are formed as byproducts. Since these impurities have properties such that are close in boiling point to hydroxyl group-containing vinyl ethers, form azeotropic compositions therewith and are close in polarity thereto, for instance, a complicated purification is required for the complete isolation to obtain pure hydroxyl group-containing vinyl ethers and cost of production of pure hydroxyl group-containing vinyl ethers is increased thereby. Consequently, the vinyl ether group-containing (meth)acrylic esters produced by using such hydroxyl group-containing vinyl ethers as starting materials become expensive. Thus, the advent of methods of producing vinyl ether group-containing (meth)acrylic esters at low cost using hydroxyl group-containing vinyl ethers as starting materials is awaited.

Another problem is that since vinyl ether group-containing (meth)acrylic esters, when produced by any of the methods (A) to (F), decompose during the process of production thereof, leading to impurity formation, peroxide formation and polymerization, it is impossible to stably produce them.

The method of producing vinyl ether group-containing (meth)acrylic esters which comprises subjecting (meth) acrylic ester and a hydroxyl group-containing vinyl ethers to transesterification is advantageous from the industrial viewpoint since it does not use any expensive or hazardous raw materials. However, it has the problem that the yields of vinyl ether group-containing (meth)acrylic esters is decreased by polymerization occurring in the reaction system. Further, there is another problem that peroxide formation due to the excess of molecular oxygen and impurity formation due to decomposition. There is a further problem that since the starting material hydroxyl group-containing vinyl ether, and the product vinyl ether group-containing (meth)acrylic ester each has a vinyl ether group, side reactions such as polymerization of the vinyl ether groups of the products and starting materials as caused by (meth)acrylic acid formed in trace amounts due to water occurring in the system and isomerization of the starting material hydroxyl group-containing vinyl ether to the corresponding 2-substituted-1,3-dioxo compound occur.

For the method of purifying the vinyl ether group-containing (meth)acrylic esters produced by such methods as mentioned above, there are known the techniques of extraction, washing with water, evaporation, distillation and column chromatography, etc. However, because of the easy radical polymerizability and cation polymerizability of vinyl ether group-containing (meth)acrylic esters, polymerization occurs in the process of purification and, further, impurity formation may easily occur as a result of decomposition. Accordingly, vinyl ether group-containing (meth)acrylic esters can hardly be said to be producible stably from the industrial viewpoint. The quality and storage stability problems of the product obtained still remain unsolved. Thus, there is room for investigation with a view to prevent the formation of impurities as a result of polymerization and decomposition of vinyl ether group-containing (meth) acrylic esters in the stages of storage, handling, production and purification thereof and thus render such vinyl ether group-containing (meth)acrylic esters fully practical for industrial use.

The present invention has been made in view of the above-mentioned state of the art. Accordingly, it is an object of the present invention to provide vinyl ether group-containing (meth)acrylic esters, which has both radical polymerizability and cation polymerizability, improved in storage stability and stability in handling without impairing its polymerizability or, in other words, provide stabilized vinyl ether group-containing (meth)acrylic esters. Another object is to provide methods of producing stabilized vinyl ether group-containing (meth)acrylic ester compositions. A further object is to provide methods of stably handing, methods of economically and stably producing and methods of purifying such vinyl ether group-containing (meth)acrylic esters.

SUMMARY OF THE INVENTION

The present inventors made investigations in various ways in search for means of improving the stability of vinyl ether group-containing (meth)acrylic esters, which have both radical polymerizability and cation polymerizability and, as a result, found that by causing a radical polymerization inhibitor to coexist with vinyl ether group-containing (meth)acrylic esters, it is possible to improve the stability of vinyl ether group-containing (meth)acrylic esters while preventing the polymerization thereof during storage or handling without impairing polymerizability of vinyl ether group-containing (meth)acrylic esters. They also found that when a basic compound is further caused to coexist on that occasion, the stability of vinyl ether group-containing (meth)acrylic esters can be more improved. Thus, they realized that by employing such compositions, it becomes possible to improve the storage stability and stability in handling thereof simply and economically to thereby render vinyl ether group-containing (meth)acrylic esters suited for a wide range of industrial use. Hereinafter, these compositions are sometimes referred to as stabilized vinyl ether group-containing (meth)acrylic ester compositions.

It is considered that vinyl ether group-containing (meth) acrylic esters are polymerized when, during storage or handling, (1) radicals are formed as a result of abstraction of hydrogen atoms on carbon atoms adjacent to vinyl ether groups or (2) radicals are formed as a result of formation of ether peroxides from vinyl ether groups. In these cases, it is meant that vinyl ether group-containing (meth)acrylic esters involved in radical formation act as initiators. The above-mentioned case (2) maybe avoided by replacing the atmosphere with nitrogen and, on this occasion, esters are to be handled in an atmosphere containing molecular oxygen to prevent polymerization of (meth)acryloyl groups due to free of oxygen. On the other hand, with vinyl ethers other than (meth)acrylic esters or with vinyl ether group-free (meth) acrylic esters, such an event as mentioned above under (1) or (2) generally will not occur. Thus, as compared with these, vinyl ether group-containing (meth)acrylic esters have insufficient stability. While those (meth)acrylic esters which have ether groups may exceptionally form radicals as a result of abstraction of hydrogen atoms on carbon atoms adjacent to ether groups, the rate of hydrogen atom abstraction in vinyl ether group-containing (meth)acrylic esters is much faster and, even when compared with such (meth) acrylic esters, vinyl ether group-containing (meth)acrylic esters are insufficient in stability.

The present inventors paid their attention to these causes leading to decreased stability of vinyl ether group-containing (meth)acrylic esters and found that the problems mentioned above can be solved successfully by the above-mentioned contrivances that have so far never been made. In an aspect, such finding has led to completion of the present invention.

The inventors further made investigations concerning how to handle vinyl ether group-containing (meth)acrylic esters and, as a result, found (1) that when the water concentration in the liquid phase containing vinyl ether group-containing (meth)acrylic esters is excessively high, vinyl ether groups tend to be decomposed or the ester moiety hydrolyzed and (meth)acrylic acids formed upon this hydrolysis may possibly cause polymerization of vinyl ether groups and (2) that when the oxygen concentration in the gaseous phase in contact with vinyl ether group-containing (meth)acrylic esters is excessively low, (meth)acryloyl groups undergo polymerization due to free of oxygen and, when the oxygen concentration in the gaseous phase is excessively high, vinyl ether groups are deteriorated. They thus realized that by restricting the water concentration in the liquid phase containing vinyl ether group-containing (meth)acrylic esters and/or the oxygen concentration in the gaseous phase in contact with vinyl ether group-containing (meth)acrylic esters to a specific range, it becomes possible to handle vinyl ether group-containing (meth)acrylic esters in a stable manner.

Furthermore, they found (3) that vinyl ether group-containing (meth)acrylic esters easily, because of their easy polymerizability, undergo quality deterioration due to polymerization and/or decomposition when subjected to irradiation with light, in particular visible rays and/or ultraviolet rays and (4) that the quality deterioration due to polymerization or decomposition upon light irradiation is influenced by molecular oxygen. They thus realized that by handling vinyl ether group-containing (meth)acrylic esters in lightproof structures, it is also possible to handle the same in a stable condition and that by restricting the molecular oxygen concentration in the gaseous phase within lightproof structures, it is possible to handle esters in a more stable condition.

They made further investigations concerning methods of producing vinyl ether group-containing (meth)acrylic esters and, as a result, found that when, in the method of producing vinyl ether group-containing (meth)acrylic esters by subjecting hydroxyl group-containing vinyl ethers and (meth) acrylic esters to transesterification reaction, hydroxyl group-containing vinyl ether compositions containing specific impurities, not completely pure hydroxyl group-containing vinyl ethers, are used as raw materials, the desired esters can be produced in an economic manner and the by product lower alcohol can be removed more easily than in the case where pure hydroxyl group-containing vinyl ethers are used as raw materials and, thus, the time required for the production of vinyl ether group-containing (meth)acrylic esters can be shortened. In addition, they found that when, in carrying out the transesterification reaction, the water content or oxygen concentration in the reaction system is restricted to a specific range and/or the reaction is carried out in lightproof structures, vinyl ether group-containing (meth) acrylic esters can be produced stably in a simple and economical manner while inhibiting polymerization. The "time required for the production" so referred to herein means the time from the point of initiation of temperature raising in the reaction system to the point when the yield of vinyl ether group-containing (meth)acrylic esters becomes constant as indicated by analysis of the reaction system using gas chromatography.

They also found that when, in purifying vinyl ether group-containing (meth)acrylic esters produced, the purification is carried out in an atmosphere such that the molecular oxygen concentration in the gaseous phase in the purification system is within a specific range, or in lightproof structures, esters can be purified stably in a simple and economical manner while preventing the formation of impurities due to polymerization and decomposition during purification. Such findings have led to completion of the present invention.

DETAILED DESCRIPTION OF THE INVENTION

A vinyl ether group-containing (meth)acrylic ester composition and a method of producing the same according to the present invention are described in the following.

The vinyl ether group-containing (meth)acrylic ester composition in the present invention comprises causing a radical polymerization inhibitor, or both of a radical polymerization inhibitor and a basic compound, to coexist with a vinyl ether group-containing (meth)acrylic ester represented by the following general formula (1):

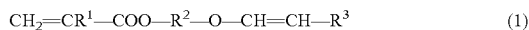

$$CH_2=CR^1-COO-R^2-O-CH=CH-R^3 \quad (1)$$

in the formula, $R^1$ represents a hydrogen atom or a methyl group, $R^2$ represents an organic residue and $R^3$ represents a hydrogen atom or an organic residue.

The vinyl ether group-containing (meth)acrylic esters in the present invention are compounds represented by the general formula (1) and having specific structures containing a vinyl ether group represented by $-O-CH=CH-R^3$ and a (meth)acryloyl group represented by $CH_2=CR^1-COO-$ within one molecule. In the practice of the present invention, such compounds may be used singly or two or more of them may be used in combination.

In the practice of the present invention, the vinyl ether group-containing (meth)acrylic esters represented by the general formula (1) may be those compounds in which the substituent represented by $R^1$ is a hydrogen atom or a methyl group, the substituent represented by $R^2$ is an organic residue and the substituent represented by $R^3$ is a hydrogen atom or an organic residue.

In the present specification, the term "organic residues" as used herein in defining compounds represented by the general formula means organic groups bound to the fundamental structures constituting these compounds.

The organic residues represented by $R^2$ in the above general formula (1) are preferably, for example, straight, branched or cyclic alkylene groups containing 2 to 20 carbon atoms, alkylene groups containing 2 to 20 carbon atoms and having at least one oxygen atom in the form of an ether linkage and/or an ester linkage within the structure thereof, and aromatic groups which contain 6 to 11 carbon atoms and may optionally be substituted. Among them, alkylene groups containing 2 to 6 carbon atoms and alkylene groups containing 4 to 10 carbon atoms and having at least one oxygen atom in the form of an ether linkage are preferred.

The organic residues represented by $R^3$ in the above general formula (1) are preferably, for example, straight, branched or cyclic alkyl groups containing 1 to 10 carbon atoms and aromatic groups which contain 6 to 11 carbon atoms and may optionally be substituted. Among them, alkyl groups containing 1 to 2 carbon atoms and aromatic groups containing 6 to 8 carbon atoms are preferred.

As typical examples of vinyl ether group-containing (meth)acrylic esters represented by the above general formula (1), specifically, the following ones are preferred: 2-Vinyloxyethyl (meth)acrylate, 3-vinyloxypropyl (meth)acrylate, 1-methyl-2-vinyloxyethyl (meth)acrylate, 2-vinyloxypropyl (meth)acrylate, 4-vinyloxybutyl (meth)acrylate, 4-vinyloxycyclohexyl (meth)acrylate, 6-vinyloxyhexyl (meth)acrylate, 4-vinyloxymethylcyclohexylmethyl (meth)acrylate, 2-(vinyloxyethoxy)ethyl (meth)acrylate and 2-(vinyloxyethoxyethoxy)ethyl (meth)acrylate.

In the practice of the present invention, methods of producing vinyl ether group-containing (meth)acrylic esters represented by the general formula (1) are preferably, for example, the method comprising subjecting a (meth)acrylic acid and a hydroxyl group-containing vinyl ether to esterification (method A), the method comprising subjecting a (meth)acrylic acid halide and a hydroxyl group-containing vinyl ether to esterification (method B), the method comprising subjecting a (meth)acrylic anhydride and a hydroxyl group-containing vinyl ether to esterification (method C), the method comprising subjecting a (meth)acrylic ester and a hydroxyl group-containing vinyl ether to transesterification (method D), the method comprising subjecting a (meth)acrylic acid and a halogen-containing vinyl ether to esterification (method E) and the method comprising subjecting a (meth)acrylic acid alkali (or alkaline earth) metal and a halogen-containing vinyl ether to esterification (method F). Among them, the method comprising subjecting a (meth)acrylic ester and a hydroxyl group-containing vinyl ether to transesterification (method D) is preferred. On that occasion, the method of producing a vinyl ether group-containing (meth)acrylic ester which is mentioned later herein is preferably applied.

In accordance with the present invention, stabilized vinyl ether group-containing (meth)acrylic ester compositions can be obtained by causing a radical polymerization inhibitor, or both of a radical polymerization inhibitor and a basic compound, to coexist with the above vinyl ether group-containing (meth)acrylic esters. The radical polymerization inhibitor and basic compound may each be used singly or a combination of two or more species.

As methods of producing vinyl ether group-containing (meth)acrylic ester compositions according to the present invention, (1) the method comprising adding a predetermined amount of a radical polymerization inhibitor, or a predetermined amount of a radical polymerization inhibitor and a predetermined amount of a basic compound, to the above vinyl ether group-containing (meth)acrylic ester, (2) the method comprising adding the vinyl ether group-containing (meth)acrylic ester to a predetermined amount of a radical polymerization inhibitor, or a predetermined amount of a radical polymerization inhibitor and a predetermined amount of a basic compound, and (3) the method comprising a combination of the above two methods are preferred. Such a production method, namely the method of causing a radical polymerization inhibitor, or both of a radical polymerization inhibitor and a basic compound, to coexist with the vinyl ether group-containing (meth)acrylic ester represented by the above general formula (1), also constitutes an aspect of the present invention.

The radical polymerization inhibitors to be used in accordance with the invention maybe those radical polymerization inhibitors in general use. Specifically, there may be preferably mentioned quinone type polymerization inhibitors such as hydroquinone, methoxyhydroquinone, benzoquinone and p-tert-butylcatechol; alkylphenol type polymerization inhibitors such as 2,6-di-tert-butylphenol, 2,4-di-tert-butylphenol, 2-tert-butyl-4,6-dimethylphenol, 2,6-di-tert-butyl-4-methylphenol and 2,4,6-tri-tert-butylphenol; amine type polymerization inhibitors such as alkylated diphenylamine, N,N'-diphenyl-p-phenylenediamine, phenothiazine, 4-hydroxy-2,2,6,6-tetramethylpiperidine, 4-benzoyloxy-2,2,6,6-tetramethylpiperidine, 1,4-dihydroxy-2,2,6,6-tetramethylpiperidine and 1-hydroxy-4-benzoyloxy-2,2,6,6-tetramethylpiperidine; copper dithiocarbamate type polymerization inhibitors such as copper dimethyldithiocarbamate, copper diethyldithiocarbamate and copper dibutyldithiocarbamate; N-oxyl type polymerization inhibitors such as 2,2,6,6-tetramethylpiperidine-N-oxyl, 4-hydroxy-2,2,6,6-tetramethylpiperidine-N-oxyl, 4-benzoyloxy-2,2,6,6-tetramethylpiperidine-N-oxyl and esters of 4-hydroxy-2,2,6,6-tetramethylpiperidine-N-oxyl; etc. Among these, quinone type polymerization inhibitors, amine type polymerization inhibitors, copper dithiocarbamate type polymerization inhibitors and N-oxyl type polymerization inhibitors are preferred radical polymerization inhibitors. Particularly preferred radical polymerization inhibitors are hydroquinone, methoxyhydroquinone, benzoquinone, p-tert-butylcatechol, phenothiazine, alkylateddiphenylamine, copper dibutyldithiocarbamate, 2,2,6,6-tetramethylpiperidine-N-oxyl, 4-hydroxy-2,2,6,6-tetramethylpiperidine-N-oxyl, esters of 4-hydroxy-2,2,6,6-tetramethylpiperidine-N-oxyl, and the like.

The level of addition of the above radical polymerization inhibitors may vary according to the species of the vinyl ether group-containing (meth)acrylic ester represented by the general formula (1) but preferably is not less than 0.00001% by weight, more preferably not less than 0.0001% by weight, still more preferably not less than 0.0002% by weigh, particularly preferably not less than 0.0005% by weight, but preferably not more than 5% by weight, more preferably not more than 1% by weight, still more preferably not more than 0.5% by weight, particularly preferably not more than 0.1% by weight, relative to said vinyl ether group-containing (meth)acrylic esters. The above range of the radical polymerization inhibitor addition level is preferred from the viewpoint of polymerization inhibition and economy.

The basic compounds to be used in accordance with the present invention are preferably, for example, alkali (alkaline earth) metal hydroxides such as lithium hydroxide, sodium hydroxide, potassium hydroxide, cesium hydroxide, magnesium hydroxide and calcium hydroxide; alkali (alkaline earth) metal carbonate salts such as lithium hydrogen carbonate, sodium hydrogen carbonate, potassium hydrogen carbonate, cesium hydrogen carbonate, magnesium hydrogen carbonate, calcium hydrogen carbonate, lithium carbonate, sodium carbonate, potassium carbonate, cesium carbonate, magnesium carbonate and calcium carbonate; alkali (alkaline earth) metal carboxylate salts such as lithium acetate, sodium acetate, potassium acetate, cesium acetate, magnesium acetate and calcium acetate; alkali (alkaline earth) metal alkoxides such as sodium methoxide, sodium ethoxide, sodium butoxide, potassium methoxide, potassium ethoxide, potassium butoxide and calcium ethoxide; amines such as ammonia, methylamine, ethylamine, butylamine, ethanolamine, dimethylamine, diethylamine, dibutylamine, diethanolamine, trimethylamine, triethylamine, tributylamine, tris(2-ethylhexyl)amine, triethanolamine, ethylenediamine, tetramethylethylenediamine, tren, 1,4-diazabicyclo[2,2,2]octane, aniline, methylaniline, dimethylaniline, pyridine, piperidine, picoline, N,N-dimethyl-p-toluidine, lutidine, quinoline, isoquinoline and collidine; etc. Preferred among these basic compounds are alkali (alkaline earth) metal hydroxides and amines. Particularly preferred basic compounds are sodium hydroxide, potassium hydroxide, tris(2-ethylhexyl)amine, tributylamine and triethanolamine.

The level of addition of the above basic compounds may vary according to the species of the vinyl ether group-containing (meth)acrylic ester represented by the general formula (1) but preferably is not less than 0.00001% by weight, more preferably not less than 0.0001% by weight, still more preferably not less than 0.0002% by weigh, particularly preferably not less than 0.0005% by weight, but preferably not more than 5% by weight, more preferably not more than 1% by weight, still more preferably not more than 0.5% by weight, particularly preferably not more than 0.1% by weight, relative to said vinyl ether group-containing (meth)acrylic esters. The above range of the basic compound addition level is preferred from the viewpoint of polymerization inhibition and economy.

By causing radical polymerization inhibitors, or both of radical polymerization inhibitors and basic compounds, to coexist with vinyl ether group-containing (meth)acrylic esters represented by the general formula (1) in accordance with the present invention, it becomes possible to stabilize the above esters more effectively. The ratio between the radical polymerization inhibitor and basic compound on that occasion may be such that each are used at an addition level within the range mentioned above.

The compositions of the present invention, namely "the vinyl ether group-containing (meth)acrylic esters and the radical polymerization inhibitors", or "the vinyl ether group-containing (meth)acrylic esters together with the radical polymerization inhibitors and the basic compounds" may be used together with other components such as additives, organic solvents and the like.

In such cases, the ratio of the vinyl ether group-containing (meth) acrylic ester is preferably not less than 50% by weight, more preferably not less than 70% by weight, still more preferably not less than 80% by weight, particularly preferably not less than 90% by weight, most preferably not less than 95% by weight, relative to the total amount of the composition.

The method of handling vinyl ether group-containing (meth)acrylic esters according to the present invention is now described.

The method of handling vinyl ether group-containing (meth)acrylic esters according to the invention is preferably (a) the mode in which the water concentration in a liquid phase containing the vinyl ether group-containing (meth) acrylic ester represented by the above general formula (1) is at a level not higher than 15% by weight, (b) the mode in which the molecular oxygen concentration in the gaseous phase in contact with the vinyl ether group-containing (meth)acrylic ester represented by the above general formula (1) is at a level of 0.01 to 15% by volume, (c) the mode in which the vinyl ether group-containing (meth)acrylic ester represented by the above general formula (1) is handled in a lightproof structure or (d) the mode in which the vinyl ether group-containing (meth)acrylic ester represented by the above general formula (1) is handled in a lightproof structure while keeping the molecular oxygen concentration in the gaseous phase within said lightproof structure at 0.01 to 22% by volume. It is also possible to appropriately combine the modes (a), (b), (c) and (d).

The term "handling" as used in the present invention means the transportation of the vinyl ether group-containing (meth)acrylic esters in tank lorries or the like; the storage in tanks, containers or the like; transfer through piping including pipes, valves, nozzles, etc.; and mixing and stirring in reaction vessels, reaction apparatuses, tanks, containers or the like. These operations may be conducted singly or two or more of them may be conducted in appropriate combination.

In handling the vinyl ether group-containing (meth) acrylic esters of the general formula (1) according to the present invention, it is preferred that radical polymerization inhibitors, or both of radical polymerization inhibitors and basic compounds be caused to coexist with the esters. As the radical polymerization inhibitors and basic compounds, there may respectively be used those specifically mentioned hereinabove.

The level of addition of the above radical polymerization inhibitors may vary according to the species of the vinyl ether group-containing (meth)acrylic ester represented by the above general formula (1) but preferably is not less than 0.0001% by weight, more preferably not less than 0.0005% by weight, still more preferably not less than 0.001% by weigh, particularly preferably not less than 0.002% by weight, but preferably not more 5% by weight, more preferably not more 1% by weight, particularly preferably not more than 0.1% by weight, relative to said vinyl ether group-containing (meth)acrylic esters. The above range of the radical polymerization inhibitor addition level is preferred from the viewpoint of yield, polymerization inhibition and economy.

The level of addition of the above basic compounds may vary according to the species of the vinyl ether group-containing (meth)acrylic ester represented by the general formula (1) but preferably is not less than 0.00001% by weight, more preferably not less than 0.0001% by weight, still more preferably not less than 0.0002% by weigh, particularly preferably not less than 0.0005% by weight, but preferably not more than 5% by weight, more preferably not more 1% by weight, still more preferably not more than 0.5% by weight, particularly preferably not more than 0.1% by weight, relative to the vinyl ether group-containing (meth)acrylic esters. The above range of the basic compound addition level is preferred from the viewpoint of yield, polymerization inhibition and economy.

In cases where the above radical polymerization inhibitors and basic compounds are caused to coexist with the esters, the ratio between the radical polymerization inhibitor and basic compound may be such that each are used at an addition level within the range mentioned above.

In handling vinyl ether group-containing (meth)acrylic esters in the above-mentioned mode (a), the water concentration in the liquid phase, namely in the liquid phase containing vinyl ether group-containing (meth)acrylic esters represented by the above general formula (1), is adjusted within a specific range. The water concentration in the liquid phase is not more than 15% by weight, preferably not more than 5% by weight, more preferably not more than 3% by weight, still more preferably not more than 1%, particularly preferably not more than 0.5% by weight. The above water concentration range is preferred from the viewpoint of stable handling.

For adjusting the water concentration in the above liquid phase to not more than 15% by weight in the production of vinyl ether group-containing (meth)acrylic esters, the following methods are preferred: the method comprising storing them promptly after purification by distillation or washing with water-insoluble solvents; the method comprising bubbling dried inert gas, such as nitrogen or argon and mixed gas composed of such inert gas and oxygen through the esters at room temperature or under warming conditions; the method comprising drying the esters with dehydrating agents such as molecular sieve, calcium chloride, magnesium sulfate, calcium sulfate or potassium carbonate, etc. These methods may appropriately be used in combination.

In handling vinyl ether group-containing (meth)acrylic esters in the above-mentioned mode (b), the molecular oxygen concentration in the gaseous phase, namely in the gaseous phase in contact with the vinyl ether group-containing (meth)acrylic esters, is adjusted within a specific range. The molecular oxygen concentration in the gaseous phase is 0.01 to 15% by volume, preferably not lower than 0.02% by volume, more preferably not lower than 0.05% by volume, but preferably not higher than 12% by volume, more preferably not higher than 10% by volume. The above molecular oxygen concentration range is preferred from the viewpoint of stable handling and economy.

The "gaseous phase (gaseous phase in contact with the vinyl ether group-containing (meth)acrylic ester)" means the gaseous phase in containers or structures, such as tank lorries or tanks, with the vinyl ether group-containing (meth) acrylic esters placed therein for handling.

As for the method of adjusting the molecular oxygen concentration in the above gaseous phase to 0.01 to 15% by volume, for example, the method comprising blowing inert gas, such as nitrogen or argon, into the gaseous phase and/or liquid phase and the method comprising blowing mixed gas composed of inert gas and oxygen into the gaseous phase and/or liquid phase are preferred.

Furthermore, in accordance with the present invention, it is preferred from the viewpoint of stable handling and economy that, in handling the vinyl ether group-containing (meth)acrylic esters, the molecular oxygen concentration in the above gaseous phase be adjusted to 0.01 to 15% by volume and the water concentration in the liquid phase containing the vinyl ether group-containing (meth)acrylic ester be adjusted to not higher than 15% by weight. In this case, the adjustment methods, the preferred molecular oxygen concentration range and the preferred water concentration range are the same as mentioned above.

In handling vinyl ether group-containing (meth)acrylic esters in the above-mentioned mode (c), handling them in lightproof structures makes stable handling possible.

The "lightproof structures" used in handling according to the present invention are structures made of lightproof materials, such as structures for transportation for example tank lorries; structures for storage for example tanks, drums, bottles and cans; structures for transfer for example pipes, nozzles and valves; and structures for mixing and stirring for example reaction vessels, tanks and containers; etc. The portion of the inside surface area of the structure to which light can reach is preferably not more than 20%, more preferably not more than 15%, still more preferably not more than 10%, particularly preferably not more than 8%, of the whole inside surface area of the structure. The "lightproof materials" as so referred to herein are materials substantially impermeable to light (visible rays, ultraviolet rays and infrared rays). Furthermore, the structure inside surface portion to which light can reach or the structure inside surface portion to which light cannot reach may be continuous or discontinuous.

The lightproof materials mentioned above include, for example, as preferred species, iron and steel such as industrial pure iron, carbon steel (JISG-SS, JISG-SC, JISG-SB, JISG-SM, JISG-SGP, JISG-STGP, JISG-STS, JISG-STB, JISG-STL, JISG-STKM, JISG-SWR, JISG-SK, JISG-SF, JISG-SC, etc.), cast iron (JISG-FC, JISG-FCD, JISG-FCM, etc.), low-alloy steel (JISG-SNC, JISG-SNCM, JISG-SCr, JISG-SCM, JISG-SACM, JISG-SCA, etc.), low-alloy cast iron (nitensil, nihard, acicular, etc.), low-nickel steel (JISG-STPL, JISG-STBL, JES-Ni, ASTM-A203, etc.), nickel steel (ASTMA353, etc.), chrome stainless steel (JISG-SUH1, JISG-SUH2, JISG-SUH3, AISI-TP501, AISI-TP503, etc.), etc.; high silicon cast iron; high nickel cast iron such as 15% Ni cast iron (Ni-Resist1, etc.), 20% Ni cast iron (Ni-Resist2, etc.), 30% Ni cast iron (Ni-Resist3, etc.), etc.; high chromium steel such as high Cr cast iron (Nirosta, etc.), high Cr—Mo cast iron, etc.

Further includes martensitic stainless steel such as 13 Crsteel (SUS403, SUS410, SUS414, SUS416, etc.), 13Cr steel (SUS420, etc.), 16Cr2Ni steel (SUS431, SUS440A, SUS440B, SUS440C, etc.), etc.; ferritic stainless steel such as 18 Cr steel (SUS420, etc.), 25Cr steel (SUS446, etc.), 13Cr—Al steel (SUS405, etc.), etc.; austenitic stainless steel such as 18-8 steel (SUS301, SUS302, SUS303, SUS304, SUS305, SUS308, SUS321, SUS347, etc.), 18-8L steel (SUS304L, etc.), 18-8Mo steel (SUS316, SUS317, etc.), 18-8MoL steel (SUS316L, etc.), 22Cr-12Ni steel (SUS309, SUS309S, etc.), 25Cr-20Ni steel (SUS310, SUS310S, SUS314, etc.), etc.; special austenitic stainless steel such as 20 alloys (Worthite, Durimet20, Carpenter20, Aloyco20, FA20, etc.), HN alloys (Chromax, etc.), etc.; Fe—Cr—Al alloys such as Fe—Cr—Al—Si alloys (Sicromal8, Sicromal9, Sicromal10, Sicromal11, Sicromal12, etc.), Fe—Cr—Al—Co alloys (KanthalA, etc.), etc.; high manganese steel such as JIS-SCMnH, etc.; copper and copper alloys such as industrial pure copper (JIS-CuP, JIS-CuB, JIS-CuT, JIS-DCuP, JIS-DCuT, etc.), Cu—Al alloys (JIS-ABP, JIS-ABB, JIS-BsTF, aluminum bronze, aluminum brass, etc.), Cu—Si alloys (JIS-SiBT, JIS-SzBC, silicon bronze, Everdur, AR alloys, Silzin bronze, etc.), Cu—Sn—P alloys (JIS-PBP, JIS-PBS, JIS-PBB, JIS-PBC, phosphor bronze, etc.), Cu—Sn—Zn alloys (JIS-BsC, bronze casting, etc.), Cu—Zn alloys (JIS-NBsP, etc.), Cu—Zn—Sn alloys (Red-Brass, etc.), Cu—Zn alloys (JIS-BsP, JIS-LBC, JIS-RBsP, brass, leaded brass, red brass, etc.), etc.; Cu—Ni alloys such as Cu—Ni 20 (cupro-nickel, JIS-CNTF2, etc.), Ni—Ag (nickel silver, German silver, JIS-NSP, JIS-SNP1, etc.), Cu—Ni 30 (cupro-nickel, JIS-CNTF3, JIS-CNP3, etc.), etc.; aluminum and aluminum alloys such as industrial pure aluminum (JIS-AlP, JIS-AlR, JIS-AlB, JIS-AlV, JIS-AlW, JIS-AlT, ALCOA-EC, ALCOA-1050, ALCOA-1060, ALCOA-1100, ALCOA-1130, ALCOA-1175, ALCOA-1260, etc.), highly pure aluminum, Al—Mn alloys (JIS-A2P3, JIS-A2T3, ALCOA-3003, etc.), high-tensile aluminum alloys (JIS-A3P, JIS-A3R, JIS-A3T, JIS-A3B, JIS-A3W, ALCOA-2014, ALCOA-2017, ALCOA-2024, ALCOA-2025, Duralumin, Super Duralumin, Y alloys, etc.), Al—Mg—Si alloys (JIS-A4F, ALCOA-6061, etc.), Al—Si alloys (JIS-AC3A, JIS-AC4ABC, ALCOA-4032, silumin casting, etc.), Al—Mg alloys (JIS-corrosion protected aluminum alloy Type 1, JIS-corrosion protected aluminum alloy Type 2, JIS-corrosion protected aluminum alloy Type 7, ALCOA-5052, ALCOA-5056, ALCOA-5083, etc.), etc.; magnesium and magnesium alloys such as industrial pure magnesium, magnesium alloys (JIS-MC, Dowmetal, Elektron, etc.), etc.; nickel such as industrial pure nickel (JIS-VNiP, JIS-VCNiP, JIS-VNiW, JIS-VCNiT, ASTM-B39, ASTM-160, ASTM-161, ASTM-162, etc.), etc.; Ni—Cr—Fe alloys such as 27A (Inconel, Colmonoy6, etc.), 27B (Incone1600, ASTM-B163, ASTM-B166, ASTM-B167, ASTM-B168, etc.), 27C, etc.; Ni—Cu alloys such as Monel (JIS-NCuT, JIS-NCuP, ASTM-B127, ASTM-B163, ASTM-B164, ASTM-B165, Monel 400, etc.), K Monel, etc.; Ni—Mo—Fe—Cr alloys such as 30A (HastelloyA, Contracid, etc.), 30B (ASTM-B333, ASTM-B335, ASTM-B494, HastelloyB, Chlorimet2, etc.), 30C (ASTM-B336, ASTM-B494, HastelloyC, Chlorimet3, etc.), 30D (HastelloyN, etc.), 30E (HastelloyF, etc.), 30F (Ni-o-nel, etc.), 30G (R-55, etc.), etc.; Ni—Cr—Cu—Mo alloys such as 31A (IlliumG, etc.), 31B (Illium98, etc.); Ni—Si alloys such as HastelloyD, etc.; cobalt alloys such as Co—Cr alloys (Stelite21, Stelite23, Stelite27, Stelite31, etc.), Co—Cr—Ni alloys (Haynes25, Haynes36, etc.), Co—Si alloys, etc.; lead and lead alloys such as industrial pure lead (JIS-PbP, JIS-PbT, JIS-PbTW, ASTM-B29, ASTM-B325, etc.), lead telluride, hard lead (JIS-HPbP, JIS-HPbT, ASTM-B23, ASTM-B32, etc.), homogen lead fusion lining, etc.; tin; zinc and zinc alloys such as industrial pure zinc (JIS-zinc plate, ASTM-B6, etc.), zinc alloys (ASTM-B69, etc.), etc.; precious metals such as silver, gold, platinum, niobium, tantalum (ASTM-B364, ASTM-B365, etc.) and platinum group and vanadium group metals; tungsten; titanium and titanium alloys such as industrial pure titanium (JIS-TP, JIS-TTP, JIS-TB, JIS-TW, ASTM-B265, ASTM-B337, ASTM-B338, ASTM-B348, ASTM-B299, ASTM-B367, ASTM-B381, etc.), titanium alloys (ASTM-B265, ASTM-B348, ASTM-B367, ASTM-B381, etc.), etc.; zirconium and zirconium alloys such as zirconium (ASTM-B349, ASTM-B350, ASTM-B351, ASTM-B352, ASTM-B353, ASTM-B356, etc.), zirconium alloys (Zircaloy-1, Zircaloy-2, Zircaloy-3, ASTM-B350, ASTM-B351, ASTM-B352, ASTM-B353, ASTM-B356, etc.), etc.; molybdenum such as ASTM-B384, ASTM-B385, ASTM-B386, ASTM-B387, etc.; chromium such as ASTM-B383, ASTM-B391, ASTM-B392, ASTM-B393, ASTM-B394, etc.; silicate products such as porcelain, earthenware, liparite, acid-resistant bricks, acid-resistant tiles, acid-resistant porcelain, silica cement, fire bricks, refractory mortar, vitreous enamel, etc.; concrete; sulfur cement; carbon and graphite products such as carbon formed products, graphite formed products, impervious carbon, impervious graphite, etc.; asbestos; synthetic resins such as opaque vinylidene chloride resin, opaque phenol resin, opaque furan resin, opaque vinyl chloride resin, opaque ethylene tetrafluoride, opaque ethylene trifluoride, opaque silicate resin, opaque polyethylene, opaque polyisobutylene, opaque polystyrene, opaque epoxy resin, opaque unsaturated polyester, opaque polyamide resin, opaque chlorinated polyether resin, opaque polycarbonate resin, opaque polyurethane resin, opaque urea resin, opaque melamine resin, etc.; asphalt; natural rubber and synthetic rubber such as opaque natural rubber, opaque natural rubber hydrochloride or chlorinated natural rubber, opaque nitrile rubber, opaque styrene rubber, opaque butadiene-isobutylene synthetic rubber, opaque polychloroprene, opaque asbestos-filled rubber sheet, opaque butyl rubber, opaque polysulfide rubber, opaque chlorosulfonated polyethylene rubber, opaque fluorine rubber, opaque silicone rubber, opaque urethane rubber, etc.; glass such as glass of which inside and/or outside is coated with opaque synthetic resin, glass of which inside and/or outside is coated with natural rubber or synthetic rubber, glass of which inside and/or outside is coated with metal, glass of which inside and/or outside is plated with metal, etc.

Among these, iron and steel, high silicon cast iron, high nickel cast iron, high chromium steel, martensitic stainless steel, ferritic stainless steel, austenitic stainless steel, special austenitic stainless steel, Fe—Cr—Al alloys, high manganese steel, copper and copper alloys, Cu—Ni alloys, aluminum and aluminum alloys, magnesium and magnesium alloys, nickel, Ni—Cr—Fe alloys, Ni—Cu alloys, Ni—Mo—Fe—Cr alloys, Ni—Cr—Cu—Mo alloys, Ni—Si alloys, cobalt alloys, lead and lead alloys, tin, zinc and zinc alloys, tungsten, titanium and titanium alloys, zirconium and zirconium alloys, molybdenum and chromium are more preferred as the lightproof material. These lightproof materials can be used singly or two or more of them may be used in combination.

In handling a vinyl ether group-containing (meth)acrylic ester represented by the above general formula (1) in the above mode (d), the ester is handled in a lightproof structure in an atmosphere such that a molecular oxygen concentration in the gaseous phase within the structure of 0.01 to 22% by volume, whereby quality degradation due to polymerization or decomposition can effectively be prevented and the vinyl ether group-containing (meth)acrylic ester can be handled in a more stable manner.

The molecular oxygen concentration in the gaseous phase within the above structures is preferably not lower than 0.02% by volume, particularly preferably not lower than 0.05% by volume, but preferably not higher than 18% by volume, particularly preferably not higher than 15% by volume. If the molecular oxygen concentration in the gaseous phase within the structures is lower than 0.01% by volume, vinyl ether group-containing (meth)acrylic esters may undergo polymerization due to free of oxygen. If the molecular oxygen concentration in the gaseous phase within the structures is higher than 22% by volume, quality degradation may occur due to polymerization or decomposition. Therefore, the above molecular oxygen concentration range is preferred from the viewpoint of quality, polymerization inhibition and economy.

It is necessary to handle the esters in lightproof structures since the quality degradation due to polymerization or decomposition mentioned above is accelerated in optically transparent structures.

Available for use in adjusting the molecular oxygen concentration in the gaseous phase within the above structures to a specific range are (a) the method comprising feeding molecular oxygen or a gas containing molecular oxygen, such as air, and an inert gas, such as nitrogen or argon, respectively to the structure and (b) the method comprising admixing molecular oxygen or a molecular oxygen-containing gas, such as air, with an inert gas, such as nitrogen or argon, in advance and then feeding the mixture to the structure, and the like. As for the gas feeding method, the gases or gas mixture is fed to one or both of the liquid phase and gaseous phase either continuously or intermittently. As for the method of maintaining the molecular oxygen concentration in the gaseous phase in the structure within a specific range, the continuous or intermittent feeding method and the method comprising initial atmosphere substitution, followed by tight closure are preferred.

In handling vinyl ether group-containing (meth)acrylic esters represented by the above general formula (1), the handling temperature is, specifically, preferably not lower than −20° C., more preferably not lower than −15° C., still more preferably not lower than −5° C., particularly preferably not lower than 0° C. Conversely, it is preferably not higher than 125° C., more preferably not higher than 100° C., still more preferably not higher than 80° C., particularly preferably not higher than 60° C. The handling pressure may be at ordinary pressure (atmospheric pressure), under pressure or under reduced pressure.

The method of producing a vinyl ether group-containing (meth)acrylic ester according to the present invention is described in the following.

The method of producing a vinyl ether group-containing (meth)acrylic ester is a method of producing a vinyl ether group-containing (meth)acrylic ester represented by the above general formula (1). The above method of producing a vinyl ether group-containing (meth)acrylic ester comprises reacting a hydroxyl group-containing vinyl ether represented by the following general formula (2):

$$R^3—CH=CH—O—R^2—OH \quad (2)$$

in the formula, $R^2$ represents an organic residue and $R^3$ represents a hydrogen atom or an organic residue, with a (meth)acrylic ester represented by the following general formula (3):

$$CH_2=CR^1—COOR^4 \quad (3)$$

in the formula, $R^1$ represents a hydrogen atom or a methyl group and $R^4$ represents an organic residue, and in which the above hydroxyl group-containing vinyl ether contains at least one compound selected from the group consisting of a divinyl ether represented by the following general formula (4):

$$R^3—CH=CH—O—R^2—O—CH=CH—R^3 \quad (4)$$

in the formula, $R^2$ represents an organic residue and the two $R^3$ groups are the same or different and each represents a hydrogen atom or an organic residue, a 2-substituted-1,3-dioxo compound represented by the following general formula (5):

in the formula, $R^2$ represents an organic residue and $R^3$ represents a hydrogen atom or an organic residue, and an unsaturated bond-containing vinyl ether represented by the following general formula (6):

$$R^3—CH=CH—O—R^5 \quad (6)$$

in the formula, $R^3$ represents a hydrogen atom or an organic residue; $R^5$ represents an organic residue containing an unsaturated bond represented by —$CR^6=CR^7$—; and $R^6$ and $R^7$ are the same or different and each represents a hydrogen atom or an organic residue. In the present specification, such production method is referred to as the production method (a).

In the above production method (a), group-containing (meth)acrylic esters can be produced economically by using hydroxyl group-containing vinyl ether compositions containing at least one compound selected from the group consisting of divinyl ethers represented by the above general formula (4), 2-substituted-1,3-dioxo compounds represented by the above general formula (5) and unsaturated bond-containing vinyl ethers represented by the above general formula (6) as a raw material (raw material composition) without using an entirely pure hydroxyl group-containing vinyl ether as a raw material and, by using such hydroxyl group-containing vinyl ether compositions, it becomes possible to remove the by product lower alcohols more easily and curtail the time for producing the vinyl ether group-containing (meth)acrylic esters as compared with the case of using the entirely pure hydroxyl group-containing vinyl ethers.

In accordance with the present invention, the starting material alcohols in the transesterification reaction are compositions containing hydroxyl group-containing vinyl ethers. The above hydroxyl group-containing vinyl ethers may be the compounds represented by the above general formula (2), in which the substituent represented by $R^3$ is a hydrogen atom or an organic residue and the substituent represented by $R^2$ is an organic residue.

The above $R^2$ and $R^3$ are the same as the $R^2$ and $R^3$ in the above general formula (1), respectively.

Typical examples of the hydroxyl group-containing vinyl ethers represented by the above general formula (2) specifically include the following preferred ones: 2-Hydroxyethyl vinyl ether, 3-hydroxypropyl vinyl ether, 4-hydroxybutyl vinyl ether, 4-hydroxycyclohexyl vinyl ether, 1,6-hexanediol monovinyl ether, 1,4-cyclohexanedimethanol monovinyl ether, diethylene glycol monovinyl ether, triethylene glycol monovinyl ether and dipropylene glycol monovinyl ether.

The raw material compositions used in the practice of the invention contain, in addition to the hydroxy-containing vinyl ethers represented by the above general formula (2), at least one compound selected from the group consisting of divinyl ethers represented by the above general formula (4), 2-substituted-1,3-dioxo compounds represented by the above general formula (5) and unsaturated bond-containing vinyl ethers represented by the above general formula (6). The divinyl ethers of the above general formula (4), 2-substituted-1,3-dioxo compound of the above general formula (5) and unsaturated bond-containing vinyl ethers of the above general formula (6) may be contained respectively singly or two or more of them may be contained.

The lower limit to the total amount of the impurities represented by the above general formulas (4), (5) and (6) is preferably not less than 0.01% by weight, more preferably not less than 0.05% by weight, still more preferably not less than 0.1% by weight, particularly preferably not less than 0.5% by weight, but preferably not more than 70% by weight, more preferably not more than 50% by weight, still more preferably not more than 30% by weight, particularly preferably not more than 20% by weight, relative to the raw material composition. The above impurity content range is preferred from the viewpoint of reaction rate, yield and economy.

The impurities represented by the above general formula (4), the above general formula (5) and the above general formula (6) are preferably contained in the starting material hydroxyl group-containing vinyl ethers of the above general formula (2). They may also occur in the reaction system, however, as a result of intentional addition to the reaction system or formation during the reaction, for instance.

In cases where the above impurities occur in the reaction system, the lower limit to the total amount thereof is preferably not less than 0.001% by weight, more preferably not less than 0.005% by weight, particularly preferably not less than 0.01% by weight, but preferably not more than 10% by weight, more preferably not more than 8% by weight, still more preferably not more than 5% by weight, particularly preferably not more than 3% by weight, relative to the reaction system. The above impurity content range is preferred from the viewpoint of reaction rate, yield and economy.

One species of the impurities to be contained in the hydroxyl group-containing vinyl ethers in the practice of the present invention is the divinyl ethers. The divinyl ethers may be those compounds represented by the above general formula (4), in which the substituent represented by $R^3$ may be the same or different and each is a hydrogen atom or an organic residue and the substituent represented by $R^2$ is an organic residue.

The above $R^2$ and $R^3$ are the same as mentioned above.

Typical examples of the divinyl ethers represented by the above general formula (4) specifically include such preferred ones as divinyl ether, ethylene glycol divinyl ether, propylene glycol divinyl ether, propanediol divinyl ether, butanediol divinyl ether, 1,4-cyclohexane divinyl ether, 1,6-hexanediol divinyl ether, 1,4-cyclohexanedimethanol divinyl ether, diethylene glycol divinyl ether, triethylene glycol divinyl ether and dipropylene glycol divinyl ether.

One species of the impurities to be contained in the hydroxyl group-containing vinyl ethers in accordance with the present invention is the 2-substituted-1,3-dioxo compounds, and may be the compounds represented by the general formula (5), in which the substituent represented by $R^3$ is a hydrogen atom or an organic residue and the substituent represented by $R^2$ is an organic residue.

The above $R^2$ and $R^3$ are the same as mentioned above.

Typical examples of the 2-substituted-1,3-dioxo compounds represented by the above general formula (5) specifically include such preferred ones as 2-methyl-1,3-dioxolane, 2,4-dimethyl-1,3-dioxolane, 2-methyl-1,3-dioxane, 2-methyl-1,3-dioxepane, 1,6-hexanediol acetaldehyde cyclic acetal, diethylene glycol acetaldehyde cyclic acetal, triethylene glycol acetaldehyde cyclic acetal and dipropylene glycol acetaldehyde cyclic acetal.

One species of the impurities to be contained in the hydroxyl group-containing vinyl ethers in accordance with the present invention is the unsaturated bond-containing vinyl ethers, and may be the compounds represented by the above general formula (6), in which the substituent represented by $R^3$ is a hydrogen atom or an organic residue and the substituent represented by $R^5$ is an organic residue containing an unsaturated bond represented by $-CR^6=CR^7-$.

The above $R^3$ is the same as mentioned above.

The organic residue represented by $R^5$ in the above general formula (6) and containing an unsaturated bond represented by $-CR^6=CR^7-$, in which $R^6$ and $R^7$ are the same or different and each is a hydrogen atom or an organic residue, is an organic residue having a structure derived from the $-R^2-OH$ group in the general formula (2) by dehydration. Specifically, when $-R^2-OH$ is $-CH_2CH_2CH_2-OH$, for instance, the organic residue represented by $R^5$ is $-CH_2CH=CH_2$ and both of $R^6$ and $R^7$ are hydrogen atoms. When $-R^2-OH$ is $-CH_2CH(OH)CH_3$, the organic residue represented by $R^5$ is $-CH_2CH=CH_2$ or $-CH=CH-CH_3$ and $R^6$ is a hydrogen atom in either case and $R^7$ is a hydrogen atom or a methyl group.

Typical examples of the unsaturated bond-containing vinyl ethers represented by the above general formula (6) specifically include such preferred ones as 2-propenyl vinyl ether, 1-propenyl vinyl ether, 3-butenyl vinyl ether and 5-hexenyl vinyl ether.

The (meth)acrylic esters, which are starting materials in the practice of the invention may be those compounds represented by the above general formula (3), in which the substituent represented by $R^1$ is a hydrogen atom or a methyl group and the substituent represented by $R^4$ is an organic residue.

The organic residues represented by $R^4$ in the above general formula (3) are preferably, for example, straight, branched or cyclic alkyl groups containing 1 to 8 carbon atoms and aromatic groups containing 6 to 10 carbon atoms, which may optionally be substituted. Among these, alkyl groups containing 1 to 4 carbon atoms are preferably used.

Typical examples of the (meth)acrylic esters represented by the above general formula (3) are, specifically, as preferred ones, lower alkyl (meth)acrylic esters such as methyl (meth)acrylate, ethyl (meth)acrylate, propyl (meth)acrylate, isopropyl (meth)acrylate, butyl (meth)acrylate, isobutyl (meth)acrylate, sec-butyl (meth)acrylate and tert-butyl (meth)acrylate. These may be used singly or in admixture.

In the practice of the invention, the transesterification reactions are preferably carried out in the presence of transesterification catalysts. The alcohols formed as reaction byproducts are preferably removed from the reaction system.

As for the reaction mole ratio between the (meth)acrylic esters and the hydroxyl group-containing vinyl ethers in the above transesterification reactions, specifically, the (meth) acrylic esters/hydroxyl group-containing vinyl ethers mole ratio is preferably within the range of 6/1 to 1/5, more preferably within the range of 5/1 to 1/3, still more preferably within the range of 4/1 to 1/2, particularly preferably within the range of 3/1 to 1/1. The above mole ratio range is preferred from the viewpoint of yield and economy.

The above transesterification catalysts are, specifically, as preferred ones, oxides such as calcium oxide, barium oxide, lead oxide, zinc oxide and zirconium oxide; hydroxides such as potassium hydroxide, sodium hydroxide, lithium hydroxide, calcium hydroxide, thallium hydroxide, tin hydroxide, lead hydroxide and nickel hydroxide; halides such as lithium chloride, calcium chloride, tin chloride, lead chloride, zirconium chloride and nickel chloride; carbonate salts such as potassium carbonate, rubidium carbonate, cesium carbonate, lead carbonate, zinc carbonate and nickel carbonate; hydrogen carbonate salts such as potassium hydrogen carbonate, rubidium hydrogen carbonate and cesium hydrogen carbonate; phosphate salts such as sodium phosphate, potassium phosphate, rubidium phosphate, lead phosphate, zinc phosphate and nickel phosphate; nitrate salts such as lithium nitrate, calcium nitrate, lead nitrate, zinc nitrate and nickel nitrate; carboxylate salts such as lithium acetate, calcium acetate, lead acetate, zinc acetate and nickel acetate; alkoxy compounds such as sodium methoxide, sodium ethoxide, potassium methoxide, potassium ethoxide, potassium tert-butoxide, calcium methoxide, calcium ethoxide, barium methoxide, barium ethoxide, tetraethoxytitanium, tetrabutoxytitanium and tetra(2-ethylhexanoxy)titanium; acetylacetonate complexes such as lithium acetylacetonate, zirconia acetylacetonate, zinc acetylacetonate, dibutoxytin acetylacetonate and dibutoxytitanium acetylacetonate; quaternary ammonium alkoxides such as tetramethylammonium methoxide, tetramethylammonium tert-butoxide and trimethylbenzylammonium ethoxide; dialkyltin compounds such as dimethyltin oxide, methylbutyltin oxide, dibutyltin oxide and dioctyltin oxide; distannoxanes such as bis(dibutyltin acetate) oxide and bis(dibutyltin laurate) oxide; and dialkyltin dicarboxylate salts such as dibutyltin diacetate and dibutyltin dilaurate. These may be used singly or two or more of them may be used in combination.

Among these transesterification catalysts, potassium carbonate, cesium carbonate, tetraethoxytitanium, tetrabutoxytitanium, tetra(2-ethylhexanoxy)titanium, zirconia acetylacetonate, dibutyltin oxide, dioctyltin oxide, bis (dibutyltin acetate) oxide, bis (dibutyltin laurate) oxide, dibutyltin diacetate and dibutyltin dilaurate are preferably used.

The level of addition of the above transesterification catalysts is, specifically, preferably not less than 0.001 mole percent, more preferably not less than 0.005 mole percent, still more preferably not less than 0.01 mole percent, particularly preferably not less than 0.05 mole percent, but preferably not more than 20 mole percent, more preferably not more than 15 mole percent, still more preferably not more than 10 mole percent, particularly preferably not more than 5 mole percent. The above range of transesterification catalyst addition level is preferred from the viewpoint of yield and economy.

As the method of removing the above by product alcohols, for example, the method comprising carrying out the reaction under reduced pressure, the method comprising carrying out the reaction using azeotropic solvents and the method comprising carrying out the reaction in the presence of adsorbents are preferred. Among these, the method comprising carrying out the reaction under reduced pressure and the method comprising carrying out the reaction using azeotropic solvents are preferred.

The above azeotropic solvents may be ones which do not adversely affect the reaction. Specifically, ethers such as diethyl ether, diisopropyl ether and dibutyl ether; aromatic hydrocarbons such as benzene, toluene and xylene; aliphatic hydrocarbons such as pentane, hexane, heptane and cyclohexane; halogenated hydrocarbons such as chloroform, methylene chloride, 1,2-dichloroethane and chlorobenzene; and the like are preferred. These azeotropic solvents may be used singly or two or more of them may be used in combination.

The level of addition of the above azeotropic solvents is, specifically, preferably not less than 0% by weight relative to the total weight of the (meth)acrylic esters represented by the general formula (3) and the hydroxyl group-containing vinyl ethers represented by the general formula (2). Conversely, it is preferably not more than 300% by weight, more preferably not more than 200% by weight, still more preferably not more than 150% by weight, particularly preferably not more than 100% by weight, relative to the total weight of the (meth)acrylic esters represented by the general formula (3) and the hydroxyl group-containing vinyl ethers represented by the general formula (2). The above range of the organic solvent addition level is preferred from the viewpoint of yield and economy.

The (meth)acrylic ester used in excess as well as the impurities represented by the above general formulas (4), (5) and (6) may also serve as the azeotropic solvent.

The reaction temperature for the above reaction is preferably not lower than the boiling point or azeotropic point of the by product alcohol. Specifically, the temperature is preferably not lower than 40° C., more preferably not lower than 50° C., particularly preferably not lower than 60° C. Conversely, it is preferably not higher than 180° C., more preferably not higher than 170° C., particularly preferably not higher than 160° C. The reaction pressure may be at ordinary pressure, under pressure or under reduced pressure. The reaction time can appropriately be selected so that the above reaction can be driven to completion.

From the viewpoint of polymerization inhibition and yield, the production of the vinyl ether group-containing (meth)acrylic esters of the above general formula (1) is preferably carried out in the presence of polymerization inhibitors. As for the polymerization inhibitors, those radical polymerization inhibitors mentioned above are preferably used, for instance, and one or two or more of them may be used.

The level of addition of the above polymerization inhibitors may vary according to the species of the (meth)acrylic ester of the general formula (3) as used and the species of the product vinyl ether group-containing (meth)acrylic ester of the general formula (1) but is preferably within the range of not less than 0.0001% by weight, more preferably not less than 0.0002% by weight, still more preferably not less than 0.0005% by weight, particularly preferably not less than 0.001% by weight, but preferably not more than 5% by weight, more preferably not more than 1% by weight, still more preferably not more than 0.5% by weight, particularly preferably not more than 0.1% by weight relative to the (meth)acrylic esters of the general formula (3). The above range of polymerization inhibitor addition level is preferred from the viewpoint of yield, polymerization inhibition and economy.

In the production method according to the invention, it is also preferable to cause basic compounds to coexist with radical polymerization inhibitors. Suited for use as basic compounds are the same ones as mentioned hereinabove, and one or two or more of them may be used.

The level of addition of the above basic compounds may vary according to the species of the starting material hydroxyl group-containing vinyl ether and the species of the product vinyl ether group-containing (meth)acrylic ester of the general formula (1) but preferably is not less than 0.0001% by weight, more preferably not less than 0.0002% by weight, still more preferably not less than 0.0005% by weight, particularly preferably not less than 0.001% by weight, but preferably not more 5% by weight, more preferably not more 1% by weight, still more preferably not more than 0.5% by weight, particularly preferably not more than 0.1% by weight, relative to the above hydroxyl group-containing vinyl ethers. The above range of basic compound is preferred from the viewpoint of yield, polymerization inhibition and economy.

As the method of producing vinyl ether group-containing (meth)acrylic esters according to the present invention, the method of producing a vinyl ether group-containing (meth)acrylic ester which comprises reacting a hydroxyl group-containing vinyl ether represented by the above general formula (2) with a (meth)acrylic ester represented by the above general formula (3) in the presence of not more than 5% by weight of water (production method (b)), the method of producing a vinyl ether group-containing (meth)acrylic ester which comprises reacting a hydroxyl group-containing vinyl ether represented by the above general formula (2) with a (meth)acrylic ester represented by the above general formula (3) in an atmosphere such that a molecular oxygen concentration is 0.01 to 10% by volume (production method (c)), the method of producing a vinyl ether group-containing (meth)acrylic ester which is carried out in a lightproof structure (production method (d)) and the method of producing a vinyl ether group-containing (meth)acrylic ester which is carried out in a lightproof structure in an atmosphere such that a molecular oxygen concentration in the gaseous phase within said lightproof structure is 0.01 to 15% by volume (production method (e)) are preferred.

Also suited are the method of producing a vinyl ether group-containing (meth)acrylic ester which comprises reacting a hydroxyl group-containing vinyl ether represented by the above general formula (2) with a (meth)acrylic ester represented by the general formula (3) in the presence of an N-nitrosophenylhydroxylamine salt represented by the following general formula (7):

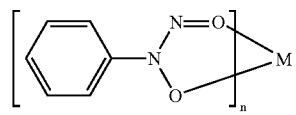

(7)

in the formula, M represents a metal atom or an ammonium group and n represents an integer equal to the valence of M (production method (f)) and the method of producing a vinyl ether group-containing (meth)acrylic ester which comprises reacting a hydroxyl group-containing vinyl ether represented by the above general formula (2) with a (meth)acrylic ester represented by the above general formula (3) in an atmosphere such that a molecular nitrogen monoxide (NO) and/or molecular nitrogen dioxide ($NO_2$) concentration in the gaseous phase in the reaction system is 0.01 to 10% by volume (production method (g)). One of these production methods may be carried out or the production methods mentioned above may be carried out in appropriate combination. It is preferred, however, that they be carried out in appropriate combination.

In the above production methods (b), (c), (f) and (g), hydroxyl group-containing vinyl ethers of the above general formula (2) and (meth)acrylic esters of the above general formula (3) are subjected to transesterification reaction. The hydroxyl group-containing vinyl ethers of the above general formula (2), the (meth)acrylic esters of the above general formula (3), the methods of subjecting these to transesterification reaction and the reactions conditions, and the like, are the same as those mentioned hereinabove. Further, in carrying out the transesterification reaction, the reaction is preferably carried out in the presence of the above-mentioned radical polymerization inhibitors or the radical polymerization inhibitors and the basic compounds. The levels of addition of the radical polymerization inhibitors and basic compounds are the same as in the production method (a).

The above production method (b) is carried out in the presence of not more than 5% by weight of water. Thus, the amount of water in the liquid phase in the reaction system is kept at not more than 5% by weight relative to the total weight of the liquid phase in the reaction system. In the above production method (b), the amount of water in the reaction system, namely in the liquid phase in the reaction system, is not more than 5% by weight, preferably not more than 3% by weight, more preferably not more than 1% by weight, relative to the total weight of the liquid phase in the reaction system. The above water content range is preferred from the viewpoint of selectivity, yield and economy.

In the above production method (c), the transesterification reaction is carried out in an atmosphere such that the molecular oxygen concentration in the gaseous phase in the reaction system is 0.01 to 10% by volume. By selecting the molecular oxygen concentration in the gaseous phase in the reaction system in the above range, the polymerization in the above reaction system can be effectively inhibited and the desired vinyl ether group-containing (meth)acrylic ester can be produced in high yields. In a preferred embodiment, the molecular oxygen concentration in the gaseous phase in the above reaction system is not less than 0.02% by volume, more preferably not less than 0.05% by volume, but preferably not more than 9% by volume, more preferably not more than 8% by volume. The above molecular oxygen concentration range is preferred from the viewpoint of yield, polymerization inhibition in reaction system, explosion avoidance and economy.

Available for adjusting the molecular oxygen concentration in the above gaseous phase to 0.01 to 10% by volume are (a) the method comprising feeding molecular oxygen or a molecular oxygen-containing gas, such as air, into a reaction vessel (vapors occurring therein) during reaction until that concentration falls within the range of 0.01 to 10% by volume relative to the volume of the gaseous phase in the reaction system, (b) the method comprising feeding molecular oxygen or a molecular oxygen-containing gas, such as air, and an inert gas, such as nitrogen or argon, respectively into a reaction vessel (vapors occurring therein) during reaction until the concentration falls within the range of 0.01 to 10% by volume relative to the volume of the gaseous phase in the reaction system, (c) the method comprising admixing molecular oxygen or a molecular oxygen-containing gas, such as air, with an inert gas, such as nitrogen or argon, in advance and feeding the mixture into a reaction vessel (vapors occurring therein) during reaction until the concentration falls within the range of 0.01 to 10% by volume relative to the volume of the gaseous phase in the reaction system, and the like.

As the methods for feeding molecular oxygen or a mixed gas containing molecular oxygen to the reaction system, it may be fed to one or both of the liquid phase and gaseous phase in the reaction system either continuously or intermittently.

In the above production method (f), the polymerization in the above reaction system can be effectively inhibited and the desired vinyl ether group-containing (meth)acrylic esters can be produced in high yield by causing N-nitrosophenylhydroxylamine salts represented by the above general formula (7) to coexist in the step of the transesterification reaction. The N-nitrosophenylhydroxylamine salts of the general formula (7) may be used singly or two or more species may be used in combination.

Referring to the above general formula (7), typical examples of the metal atom represented by M are aluminum, copper, iron(III), tin, zinc, magnesium and the like. Among these, aluminum is particularly preferred.

The level of addition of the above N-nitrosophenylhydroxylamine salts is preferably not less than 0.00001% by weight, more preferably not less than 0.0001% by weight, still more preferably not less than 0.0002% by weight, particularly preferably not less than 0.0005% by weight, but preferably not more5% by weight, more preferably not more than 1% by weight, still more preferably not more than 0.5% by weight, particularly preferably not more than 0.1% by weight, relative to the (meth)acrylic esters represented by the above general formula (3). The above range of N-nitrosophenylhydroxylamine salt addition level is preferred from the viewpoint of yield, polymerization inhibition in reaction system, and economy.

In the above production method (g), the polymerization in the above reaction system can be effectively inhibited and the desired vinyl ether group-containing (meth)acrylic esters can be produced in high yields by carrying out the transesterification reaction in an atmosphere such that the molecular nitrogen monoxide (NO) and/or molecular nitrogen dioxide ($NO_2$) concentration in the gaseous phase in the reaction system is 0.01 to 10% by volume.

The molecular nitrogen monoxide (NO) and/or molecular nitrogen dioxide ($NO_2$) concentration in the gaseous phase in the above reaction system is preferably not less than 0.01% by volume, more preferably not less than 0.02% by volume, still more preferably not less than 0.05% by volume, but preferably not more than 10% by volume, more preferably not more than 9% by volume, still more preferably not more than 8% by volume. The above range of molecular nitrogen monoxide (NO) and/or molecular nitrogen dioxide ($NO_2$) concentration is preferred from the viewpoint of yield, polymerization inhibition in reaction system, explosion avoidance, and economy.

For adjusting the molecular nitrogen monoxide (NO) and/or molecular nitrogen dioxide ($NO_2$) concentration in the above gaseous phase to 0.01 to 10% by volume, there are available, (a) the method comprising feeding a gas containing molecular nitrogen monoxide (NO) and/or molecular nitrogen dioxide ($NO_2$) into a reaction vessel (vapors occurring therein) during reaction until the concentration falls within 0.01 to 10% by volume relative to the volume of the gaseous phase in the reaction system, (b) the method comprising feeding molecular nitrogen monoxide (NO) and/or molecular nitrogen dioxide ($NO_2$) and an inert gas, such as nitrogen or argon, respectively into a reaction vessel (vapors occurring therein) during reaction until the concentration falls within 0.01 to 10% by volume relative to the volume of the gaseous phase in the reaction system, and (c) the method comprising admixing molecular nitrogen monoxide (NO) and/or molecular nitrogen dioxide ($NO_2$) with an inert gas, such as nitrogen or argon, in advance and feeding the mixture into a reaction vessel (vapors occurring therein) during reaction until the concentration falls within 0.01 to 10% by volume relative to the volume of the gaseous phase in the reaction system.

As the method for feeding molecular nitrogen monoxide (NO) and/or molecular nitrogen dioxide ($NO_2$), or a mixed gas containing molecular nitrogen monoxide (NO) and/or molecular nitrogen dioxide ($NO_2$) to the reaction system, it may be fed to one or both of the liquid phase and gaseous phase in the reaction system either continuously or intermittently.

The term "production" as used herein referring to the above production methods (d) and (e) includes, within the meaning thereof, the steps of raw materials charging, reaction, reaction solution transfer and so forth. These steps may be carried out independently or two or more of them may be carried in appropriate combination. Among these, the raw materials charging step and the reaction step, in particular, are meant by the term.

The above production methods (d) and (e) can be applied, for example, in carrying out the above-mentioned production methods A to F. Among these, the production method which comprises subjecting (meth)acrylic esters and hydroxyl group-containing vinyl ethers to transesterification reaction (production method D) is preferred from the industrial viewpoint. As the hydroxyl group-containing vinyl ethers and (meth)acrylic esters, the same ones as those hydroxyl group-containing vinyl ethers represented by the general formula (2) and those (meth)acrylic esters represented by the general formula (3), and the like are preferred. The method of subjecting these to transesterification reaction and the reaction conditions may be the same as mentioned referring to the production methods mentioned above, for instance.

In cases where the mode of the above production methods (d) and (e) are applied to the production methods A to F, it is preferred in each case that radical polymerization inhibitors and/or basic compounds be caused to coexist. Furthermore, in carrying out the transesterification reaction, the reaction is preferably carried out in the presence of the above-mentioned radical polymerization inhibitors or the radical polymerization inhibitors and the basic compounds.

The level of addition of the radical polymerization inhibitors may vary according to the species of the starting material (meth)acrylic compound, such as (meth)acrylic acid, (meth)acrylic halide, (meth)acrylic anhydride, (meth)acrylic ester, (meth)acrylic acid alkali (or alkaline earth) metal salt or the like, and the level of addition of the above basic compounds may vary according to the species of the starting material vinyl ether, such as hydroxyl group-containing vinyl ether, halogen-containing vinyl ether or the like. However, they are the same as in the production method (a).

According to the above production method (d), vinyl ether group-containing (meth)acrylic esters represented by the above general formula (1) can be produced in a stable manner by producing them in lightproof structures. As the lightproof structures used in production, there may be mentioned structures made of lightproof materials such as reaction vessels, reaction apparatus, mixing apparatus, tanks, pipes, nozzles, valves and the like for the production purpose. The inside surface area of the structures to which light can reach is the same as mentioned above. The lightproof materials are also preferably the same ones as mentioned above. According to the above production method (e), vinyl ether group-containing (meth)acrylic esters represented by the above general formula (1) can be produced in a more stable manner by producing them in lightproof structures in an atmosphere such that the molecular oxygen concentration in the gaseous phase within said lightproof structures is 0.01 to 15% by volume.

In this manner, by carrying out the reaction while adjusting the molecular oxygen concentration in the gaseous phase within the lightproof structures to 0.01 to 15% by volume, it becomes possible to effectively inhibit the polymerization of vinyl ether group-containing (meth)acrylic esters in the liquid phase and/or gaseous phase as well as the formation of impurities and of peroxides, hence it becomes possible to produce the desired vinyl ether group-containing (meth) acrylic esters in high yields.

The molecular oxygen concentration in the gaseous phase within the above lightproof structures is generally 0.01 to 15% by volume. Preferably, however, it is not less than 0.02% by volume, particularly preferably not less than 0.05% by volume, but preferably not more than 12% by volume, particularly preferably not more than 10% by volume. If the molecular oxygen concentration within the gaseous phase in the lightproof structures is less than 0.01% by volume, the starting material (meth)acrylic compounds and the vinyl ether group-containing (meth)acrylic esters may undergo polymerization due to free of oxygen. If the molecular oxygen concentration in the gaseous phase within the structures is higher than 15% by volume, the formation of impurities and of peroxides and the polymerization of the vinyl ether group-containing (meth)acrylic esters may occur. Therefore, the above molecular oxygen concentration range is preferred from the viewpoint of yield, polymerization inhibition, and economy.

The above-mentioned formation of impurities and of peroxides and polymerization of vinyl ether group-containing (meth)acrylic esters are more accelerated in structures permeable to light and, therefore, it is necessary to carry out the production inside lightproof structures.

In adjusting the molecular oxygen concentration in the gaseous phase within the lightproof structures to 0.01 to 15% by volume, those methods of adjusting the molecular oxygen concentration mentioned hereinabove can be applied. As for the gas feeding method, the gas may be fed to one or both of the liquid phase and gaseous phase either continuously or intermittently in each step of the production process.

The vinyl ether group-containing (meth)acrylic esters of the general formula (1) produced by the above production methods can be obtained by purifying the reaction solution.

As methods of purifying the vinyl ether group-containing (meth)acrylic esters represented by the above general formula (1), there may preferably be applied, for example, the method of purifying a vinyl ether group-containing (meth) acrylic ester which is carried out in an atmosphere such that the molecular oxygen concentration in the gaseous phase in the purification system is 0.01 to 10% by volume (purification method (a)), the method of purifying vinyl ether group-containing (meth)acrylic esters which is carried out in a lightproof structure in an atmosphere such that the molecular oxygen concentration in the gaseous phase in the purification system is 0.01 to 15% by volume (purification method (b)) and a combination of these. The above-mentioned purification method (a) and purification method (b) constitute a further aspect of the present invention.

The methods of purifying vinyl ether group-containing (meth)acrylic esters according to the invention are described below.

The above term "purification" used herein means procedures after which the vinyl ether group-containing (meth) acrylic esters represented by the general formula (1) have improved concentration and/or purity as compared with the value before that procedure. More specifically, procedures include raw materials recovery, catalysts recovery, neutralization, filtration, decantation, extraction, water washing, evaporation, distillation, column chromatography and other procedures. The above procedures may be performed singly or two or more may be performed in appropriate combination. Among them, the distillation procedure is particularly preferred.

As the "lightproof structures" used in the above purification, there may be mentioned structures made of lightproof materials such as distillation vessels, distillation towers, rectification towers, distillation apparatus, separation apparatus, filtration apparatus, mixing apparatus, tanks, pipes, nozzles, valves and the like, for the purification purpose. The inside surface area of the structures to which light can reach is the same as mentioned above. The lightproof materials are also preferably the same ones as mentioned above.

In the above purification method (a), the impurity formation due to polymerization and decomposition in the above process of purification can be effectively prevented and the desired vinyl ether group-containing (meth)acrylic esters can be purified stably in simple and economical manners by carrying out the purification procedure in an atmosphere such that the molecular oxygen concentration in the gaseous phase in the purification system is 0.01 to 10% by volume.

The molecular oxygen concentration in the gaseous phase in the above purification system is 0.01 to 10% by volume. Preferably, however, it is not less than 0.02% by volume, particularly preferably not less than 0.05% by volume, but preferably not more than 9% by volume, particularly preferably not more than 8% by volume. The above molecular oxygen concentration range is preferred from the viewpoint of yield, polymerization inhibition, impurity formation prevention and economy.

In adjusting the molecular oxygen concentration to 0.01 to 10% by volume, the above-mentioned methods of adjusting the molecular oxygen concentration can be applied. As for the methods of gas feeding to the purification system, the gas may be fed to one or both of the liquid phase and gaseous phase in the purification system either continuously or intermittently.

In the above purification method (b), the impurity formation due to polymerization and decomposition in the above process of purification can be effectively prevented and the desired vinyl ether group-containing (meth)acrylic esters can be purified stably in simple and economical manners by carrying out the purification procedure in lightproof structures in an atmosphere such that the molecular oxygen concentration in the gaseous phase in the purification system is 0.01 to 15% by volume.

The molecular oxygen concentration in the gaseous phase in the above purification system is 0.01 to 15% by volume. Preferably, however, it is not less than 0.02% by volume, particularly preferably not less than 0.05% by volume, but preferably not more than 12% by volume, particularly preferably not more than 10% by volume. The above molecular oxygen concentration range is preferred from the viewpoint of yield, polymerization inhibition, and economy.

In adjusting the molecular oxygen concentration in the gaseous phase in the above purification system to 0.01 to 15% by volume and in gas feeding, the same methods as in the purification method (a) can be applied.

As the use of the vinyl ether group-containing (meth) acrylic ester compositions according to the invention and of the vinyl ether group-containing (meth)acrylic esters produced and purified according to the invention, they can be used in a wide range, for example as raw materials in the medicinal and agricultural chemicals, as synthetic intermediates and further as polymerizable materials.

The present invention, which has the constitution mentioned above, can improve the stability of vinyl ether group-containing (meth)acrylic esters by preventing the polymerization of the vinyl ether group-containing (meth)acrylic esters during storage and handling thereof without impairing the polymerizability thereof and thus makes it possible to handle the vinyl ether group-containing (meth)acrylic esters in a stable manner. It further makes it possible to produce and purify vinyl ether group-containing (meth)acrylic esters in a simple, economical and stable manner while preventing the formation of impurities due to polymerization and decomposition in the process of production or purification of the vinyl ether group-containing (meth)acrylic esters.

EXAMPLES

The following examples illustrate the present invention in further detail. They are, however, by no means limitative of the scope of the invention.

Example 1

A vinyl ether group-containing (meth)acrylic ester composition was prepared by adding 10 mg of methoxyhydroquinone, a radical polymerization inhibitor, to 100 g of 2-vinyloxyethyl acrylate. The composition was placed in a sealed container and stored at 50° C. for 120 days. Thereafter, as results of analyses by visual observation and by an HLC-8120 GPC type gel permeation chromatography (product of Tosoh; hereinafter referred to as "GPC") with tetrahydrofuran as the carrier, neither discoloration nor high-molecular compound formation was observed.

Examples 2 to 12

The same procedure as in Example 1 was followed except that the vinyl ether group-containing (meth)acrylic ester and/or radical polymerization inhibitor used differed in species and/or the amounts thereof were varied. The species used, the amounts thereof and the results of visual observation and GPC are shown in Table 1.

TABLE 1

|  | Example | | | | | | |
|---|---|---|---|---|---|---|---|
|  | 1 | 2 | 3 | 4 | 5 | 6 | 7 |
| Vinyl ether group-containing (meth) acrylic ester | VEA | VEA | VEM | VEM | VEEA | VEEA | VEEM |
| (g) | 100 | 100 | 100 | 100 | 100 | 100 | 100 |
| Radical polymerization inhibitor | MEHQ | PTZ | HQ | TEMPO | MEHQ | TEMPO | MEHQ |
| (mg) | 10 | 10 | 10 | 10 | 10 | 10 | 10 |
| Storage temperature | 50° C. | 50° C. | 50° C. | 50° C. | 50° C. | 50° C. | 50° C. |
| Number of days of storage | 120 days | 120 days | 120 days | 120 days | 120 days | 120 days | 120 days |
| Visual observation | No change | No change | No change | No change | No change | No change | No change |
| Result of GPC analysis | No polymer formed | No polymer formed | No polymer formed | No polymer formed | No polymer formed | No polymer formed | No polymer formed |

|  | Example | | | | |
|---|---|---|---|---|---|
|  | 8 | 9 | 10 | 11 | 12 |
| Vinyl ether group-containing (meth) acrylic ester | VEEM | VBA | VBA | VBM | VBM |
| (g) | 100 | 100 | 100 | 100 | 100 |
| Radical polymerization inhibitor | TEMPO | PTZ | TEMPO | MEHQ | PTZ |
| (mg) | 10 | 10 | 10 | 10 | 10 |
| Storage temperature | 50° C. | 50° C. | 50° C. | 50° C. | 50° C. |
| Number of days of storage | 120 days | 120 days | 120 days | 120 days | 120 days |
| Visual observation | No change | No change | No change | No change | No change |
| Result of GPC analysis | No polymer formed | No polymer formed | No polymer formed | No polymer formed | No polymer formed |

The symbols used in Table 1 are as follows.

As regards the vinyl ether group-containing (meth)acrylic esters, VEA stands for 2-vinyloxyethyl acrylate, VEM for 2-vinyloxyethylmethacrylate, VEEA for 2-(vinyloxyethoxy) ethyl acrylate, VEEM for 2-(vinyloxyethoxy) ethyl methacrylate, VBA for 4-vinyloxybutyl acrylate, and VBM for 4-vinyloxybutyl methacrylate. As regards the radical polymerization inhibitors, MEHQ stands for methoxyhydroquinone, PTZ for phenothiazine, HQ for hydroquinone, and TEMPO for 2,2,6,6-tetramethylpiperidine-N-oxyl.

Example 13

A vinyl ether group-containing (meth)acrylic ester composition was prepared by adding 5 mg of methoxyhydroquinone, a radical polymerization inhibitor, and 5 mg of sodium hydroxide, a basic compound, to 100 g of 2-vinyloxyethyl acrylate, and the composition was placed in a sealed container and stored at 50° C. for 120 days. As results of analyses by visual observation and GPC, neither discoloration nor high-molecular compound formation was observed.

Examples 14 to 24

The same procedure as in Example 13 was followed except that the vinyl ether group-containing (meth)acrylic ester and/or radical polymerization inhibitor and/or basic compound used differed in species and/or the amounts thereof were varied. The species used, the amounts thereof and the results of visual observation and GPC are shown in Table 2.

Comparative Examples 1 to 6

A 100-g portion of each of radical polymerization inhibitor-free vinyl ether group-containing (meth)acrylic ester was placed in a sealed container and stored at 50° C. An hour later, all the vinyl ether group-containing (meth)acrylic esters used began to become turbid and, after 5 hours, became white solids insoluble in tetrahydrofuran. The vinyl ether group-containing (meth)acrylic esters used were as shown in Table 3. The symbols used in Table 3 are the same as above.

TABLE 2

| | Example | | | | | | |
|---|---|---|---|---|---|---|---|
| | 13 | 14 | 15 | 16 | 17 | 18 | 19 |
| Vinyl ether group-containing (meth) acrylic ester | VEA | VEA | VEM | VEM | VEEA | VEEA | VEEM |
| (g) | 100 | 100 | 100 | 100 | 100 | 100 | 100 |
| Radical polymerization inhibitor | MEHQ | MEHQ | MEHQ | MEHQ | MEHQ | MEHQ | MEHQ |
| (mg) | 5 | 5 | 5 | 5 | 5 | 5 | 5 |
| Basic compound | NaOH | TEHA | NaOH | TEHA | NaOH | TEHA | NaOH |
| (mg) | 5 | 5 | 5 | 5 | 5 | 5 | 5 |
| Storage temperature | 50° C. | 50° C. | 50° C. | 50° C. | 50° C. | 50° C. | 50° C. |
| Number of days of storage | 120 days | 120 days | 120 days | 120 days | 120 days | 120 days | 120 days |
| Visual observation | No change | No change | No change | No change | No change | No change | No change |
| Result of GPC analysis | No polymer formed | No polymer formed | No polymer formed | No polymer formed | No polymer formed | No polymer formed | No polymer formed |

| | Example | | | | |
|---|---|---|---|---|---|
| | 20 | 21 | 22 | 23 | 24 |
| Vinyl ether group-containing (meth) acrylic ester | VEEM | VBA | VBA | VBM | VBM |
| (g) | 100 | 100 | 100 | 100 | 100 |
| Radical polymerization inhibitor | MEHQ | MEHQ | MEHQ | MEHQ | MEHQ |
| (mg) | 5 | 5 | 5 | 5 | 5 |
| Basic compound | TEHA | NaOH | TEHA | NaOH | TEHA |
| (mg) | 5 | 5 | 5 | 5 | 5 |
| Storage temperature | 50° C. | 50° C. | 50° C. | 50° C. | 50° C. |
| Number of days of storage | 120 days | 120 days | 120 days | 120 days | 120 days |
| Visual observation | No change | No change | No change | No change | No change |
| Result of GPC analysis | No polymer formed | No polymer formed | No polymer formed | No polymer formed | No polymer formed |

The symbols used in Table 2 are as follows.

As regards the basic compounds, NaOH stands for sodium hydroxide and TEHA for tris(2-ethylhexyl)amine. The other symbols are the same as in Table 1.

TABLE 3

| | Comparative Example | | | | | |
|---|---|---|---|---|---|---|
| | 1 | 2 | 3 | 4 | 5 | 6 |
| Vinyl ether group-containing (meth) acrylic ester | VEA | VEM | VEEA | VEEM | VBA | VBM |
| (g) | 100 | 100 | 100 | 100 | 100 | 100 |
| Radical polymerization inhibitor (mg) | — | — | — | — | — | — |
| Basic compound (mg) | — | — | — | — | — | — |
| Storage temperature | 50° C. | 50° C. | 50° C. | 50° C. | 50° C. | 50° C. |
| Storage time | 5 hrs | 5 hrs | 5 hrs | 5 hrs | 5 hrs | 5 hrs |
| Result | THF-insoluble solid formed | THF-insoluble solid formed | THF-insoluble solid formed | THF-insoluble solid formed | THF-insoluble solid formed | THF-insoluble solid formed | except that radical polymerization inhibitor-free butyl methacrylate was used in Comparative Example 7 and radical polymerization inhibitor-free 2-(methoxyethoxy)ethyl methacrylate in Comparative Example 8. Butyl methacrylate and 2-(methoxyethoxy) ethyl methacrylate both showed no turbidity for 10 hours, without formation of any substance insoluble in tetrahydrofuran.

Example 25

A vinyl ether group-containing (meth)acrylic ester composition was prepared by adding 10 mg of methoxyhydroquinone, a radical polymerization inhibitor, to 100 g of 2-(vinyloxyethoxy)ethyl acrylate, and the composition was placed in a sealed container and stored at 100° C. for 12 hours. Until 5 hours later, no solid matter was detected by visual observation. After 12 hours, however, the composition became a solid insoluble in tetrahydrofuran.

Example 26

The same procedure as in Example 25 was followed except that 2-(vinyloxyethoxy) ethyl methacrylate was used in lieu of 2-(vinyloxyethoxy)ethyl acrylate. Until 5 hours later, no solid matter was detected by visual observation. After 12 hours, however, the composition became a solid insoluble in tetrahydrofuran.

Comparative Examples 9 and 10

The same procedure as in Example 25 was followed except that 2-(methoxyethoxy)ethyl acrylate was used in Comparative Example 9 and 2-(methoxyethoxy)ethyl methacrylate in Comparative Example 10. With both 2-(methoxyethoxy)ethyl acrylate and 2-(methoxyethoxy)ethyl methacrylate, no tetrahydrofuran-insoluble matter formation was observed.

Example 27

The same procedure as in Example 13 was followed except that 100 g of toluene was added following the production of the composition obtained by Example 13. As results of analyses by visual observation and GPC, neither discoloration nor high-molecular compound formation was observed.

Example 28

The same procedure as in Example 13 was followed except that 50 g of toluene was added following the production of the composition obtained by Example 13. As results of analyses by visual observation and GPC, neither discoloration nor high-molecular compound formation was observed.

Example 29

The same procedure as in Example 13 was followed except that 25 g of toluene was added following the production of the composition obtained by Example 13. As results of analyses by visual observation and GPC, neither discoloration nor high-molecular compound formation was observed.

Example 30

The same procedure as in Example 13 was followed except that 10 g of toluene was added following the production of the composition obtained by Example 13. As results of analyses by visual observation and GPC, neither discoloration nor high-molecular compound formation was observed.

Example 31

The same procedure as in Example 13 was followed except that 5 g of toluene was added following the production of the composition obtained by Example 13. As results of analyses by visual observation and GPC, neither discoloration nor high-molecular compound formation was observed.

Each vinyl ether group-containing (meth)acrylic ester used in the following Examples 32 to 55 was synthesized by the above-mentioned production method D and then purified by distillation under reduced pressure.

Example 32

A 100-g portion of 2-vinyloxyethyl acrylate having a water content of 0.01% by weight as determined by using a model MKS 510 Karl Fischer moisture meter (product of Kyoto Denshi Kogyo, hereinafter referred to as "moisture meter"; indicator: Hydranal Composite 5K (product of R&H Laborchemikalien GmbH & Co. KG); solvent: Dehydrated Solvent KT (product of Mitsubishi Chemical)) was added to a test tube and 10 mg of methoxyhydroquinone was further added. After mixing, a 21% (by volume) oxygen gas (the balance being nitrogen) was passed through the gaseous phase in the test tube for 10 minutes and then the test tube was tightly stoppered.

The test tube prepared in the above manner was shaken on an oil bath maintained at 80° C. for 40 days, followed by visual observation and by analysis using a model GC-1700 gas chromatograph (product of Shimadzu; hereinafter this chromatographic analysis is referred to as "GC"), GPC and analysis using a model RQ Flex peroxide assaying instrument (product of Merck Co. Ltd.; hereinafter this analysis is referred to as "RQ assay"). While neither impurity formation nor high-molecular substance formation was observed, a peroxide content of 2 ppm was detected.

Examples 33 to 55

The same procedure as in Example 32 was repeated except that the vinyl ether group-containing (meth)acrylic ester and/or radical polymerization inhibitor used differed in species and/or the amounts thereof were varied and that the oxygen concentration and/or water content was varied and further that a basic compound was used or not used. The species used, the amounts thereof, the storage temperature, the number of days of storage, and the results of visual observation, GC, GPC and RQ assay are shown in Tables 4 to 6. The symbols used in Tables 4 to 6 are the same as in Table 1 and Table 2.

TABLE 4

| | Example | | | | | | | |
|---|---|---|---|---|---|---|---|---|
| | 32 | 33 | 34 | 35 | 36 | 37 | 38 | 39 |
| Vinyl ether group-containing (meth) acrylic ester | VEA | VEM | VEEA | VEEA | VEEM | VEEM | VBA | VBM |
| (g) | 100 | 100 | 100 | 100 | 100 | 100 | 100 | 100 |
| Radical polymerization inhibitor | MEHQ | MEHQ | MEHQ | MEHQ | MEHQ | MEHQ | MEHQ | MEHQ |
| (mg) | 10 | 10 | 10 | 5 | 10 | 5 | 10 | 10 |
| Basic compound | — | — | — | TEHA | — | TEHA | — | — |
| (mg) | — | — | — | 5 | — | 5 | — | — |
| Oxygen concentration | 21 vol % | 21 vol % | 21 vol % | 21 vol % | 21 vol % | 21 vol % | 21 vol % | 21 vol % |
| Water content | 0.01 wt % | 0.05 wt % | 0.01 wt % | 3 wt % | 0.8 wt % | 5 wt % | 0.1 wt % | 1 wt % |
| Storage temperature | 80° C. | 80° C. | 80° C. | 80° C. | 80° C. | 80° C. | 80° C. | 80° C. |
| Number of days of storage | 40 days | 40 days | 40 days | 40 days | 40 days | 40 days | 40 days | 40 days |
| Visual observation | No change | No change | No change | No change | No change | No change | No change | No change |
| Result of GC analysis | 1% purity decrease | 1% purity decrease | 1% purity decrease | 3% purity decrease | 2% purity decrease | 3% purity decrease | 2% purity decrease | 2% purity decrease |
| Result of GPC analysis | No polymer formed | No polymer formed | No polymer formed | No polymer formed | No polymer formed | No polymer formed | No polymer formed | No polymer formed |
| Result of RQ assay | 2 ppm | 2 ppm | 2 ppm | 2 ppm | 2 ppm | 2 ppm | 2 ppm | 2 ppm |

TABLE 5

| | Example | | | | | | | |
|---|---|---|---|---|---|---|---|---|
| | 40 | 41 | 42 | 43 | 44 | 45 | 46 | 47 |
| Vinyl ether group-containing (meth) acrylic ester | VEA | VEM | VEEA | VEEA | VEEM | VEEM | VBA | VBM |
| (g) | 100 | 100 | 100 | 100 | 100 | 100 | 100 | 100 |
| Radical polymerization inhibitor | MEHQ | MEHQ | MEHQ | MEHQ | MEHQ | MEHQ | MEHQ | MEHQ |
| (mg) | 10 | 10 | 10 | 5 | 10 | 5 | 10 | 10 |
| Basic compound | — | — | — | TEHA | — | TEHA | — | — |
| (mg) | — | — | — | 5 | — | 5 | — | — |
| Oxygen concentration | 1.5 vol % | 0.8 vol % | 5 vol % | 10 vol % | 7 vol % | 9 vol % | 7 vol % | 0.5 vol % |
| Water content | 7 wt % | 7 wt % | 7 wt % | 7 wt % | 7 wt % | 7 wt % | 7 wt % | 7 wt % |
| Storage temperature | 80° C. | 80° C. | 80° C. | 80° C. | 80° C. | 80° C. | 80° C. | 80° C. |
| Number of days of storage | 40 days | 40 days | 40 days | 40 days | 40 days | 40 days | 40 days | 40 days |
| Visual observation | No change | No change | No change | No change | No change | No change | No change | No change |
| Result of GC analysis | 3% purity decrease | 3% purity decrease | 3% purity decrease | 3% purity decrease | 3% purity decrease | 3% purity decrease | 3% purity decrease | 3% purity decrease |
| Result of GPC analysis | No polymer formed | No polymer formed | No polymer formed | No polymer formed | No polymer formed | No polymer formed | No polymer formed | No polymer formed |
| Result of RQ assay | Not detected | Not detected | Not detected | Not detected | Not detected | Not detected | Not detected | Not detected |

TABLE 6

| | Example | | | | | | | |
|---|---|---|---|---|---|---|---|---|
| | 48 | 49 | 50 | 51 | 52 | 53 | 54 | 55 |
| Vinyl ether group-containing (meth) acrylic ester | VEA | VEM | VEEA | VEEA | VEEM | VEEM | VBA | VBM |
| (g) | 100 | 100 | 100 | 100 | 100 | 100 | 100 | 100 |
| Radical polymerization inhibitor | MEHQ | MEHQ | MEHQ | MEHQ | MEHQ | MEHQ | MEHQ | MEHQ |
| (mg) | 10 | 10 | 10 | 5 | 10 | 5 | 10 | 10 |
| Basic compound | — | — | — | TEHA | — | TEHA | — | — |
| (mg) | — | — | — | 5 | — | 5 | — | — |
| Oxygen concentration | 7 vol % | 7 vol % | 7 vol % | 7 vol % | 7 vol % | 7 vol % | 7 vol % | 7 vol % |
| Water content | 0.01 wt % | 0.01 wt % | 0.01 wt % | 0.01 wt % | 0.01 wt % | 0.01 wt % | 0.01 wt % | 0.01 wt % |
| Storage temperature | 80° C. | 80° C. | 80° C. | 80° C. | 80° C. | 80° C. | 80° C. | 80° C. |
| Number of days of storage | 40 days | 40 days | 40 days | 40 days | 40 days | 40 days | 40 days | 40 days |
| Visual observation | No change | No change | No change | No change | No change | No change | No change | No change |
| Result of GC analysis | No change | No change | No change | No change | No change | No change | No change | No change |
| Result of GPC analysis | No polymer formed | No polymer formed | No polymer formed | No polymer formed | No polymer formed | No polymer formed | No polymer formed | No polymer formed |
| Result of RQ assay | Not detected | Not detected | Not detected | Not detected | Not detected | Not detected | Not detected | Not detected |

Example 56

2-Vinyloxyethyl acrylate (100 g), 5 mg of methoxyhydroquinone and 5 mg of tris (2-ethylhexyl) amine were added to a 200-mL SUS 316container used as a lightproof structure. After mixing up, the gaseous phase in the container was completely substituted with a 7% (by volume) oxygen gas (the balance being nitrogen), followed by tight closure. The container was stored outdoors in an applicants' research laboratory at Suita, Osaka, Japan for 180 days starting from Apr. 1, 2000, followed by visual observation, GC, GPC and RQ assay. No deterioration in quality was observed, namely neither impurity formation, nor high molecular substance formation nor peroxide formation was detected.

Examples 57 to 74

The same procedure as in Example 56 was repeated except that the vinyl ether group-containing (meth)acrylic ester and/or radical polymerization inhibitor and/or basic compound used differed in species and/or the amounts thereof were varied and the oxygen concentration was varied. The species used, the amounts thereof and the results of visual observation, GC, GPC and RQ assay are shown in Table 7 and Table 8. The symbols used in Tables 7 and 8 are the same as in Tables 1 and 2.

TABLE 7

| | Example | | | | | | | | |
|---|---|---|---|---|---|---|---|---|---|
| | 56 | 57 | 58 | 59 | 60 | 61 | 62 | 63 | 64 |
| Vinyl ether group-containing (meth) acrylic ester (g) | VEA | VEA | VEA | VEM | VEM | VEM | VEEA | VEEA | VEEA |
| | 100 | 100 | 100 | 100 | 100 | 100 | 100 | 100 | 100 |
| Radical polymerization inhibitor (mg) | MEHQ | MEHQ | PTZ | MEHQ | PTZ | MEHQ | MEHQ | MEHQ | PTZ |
| | 5 | 10 | 10 | 5 | 10 | 10 | 5 | 10 | 10 |
| Basic compound (mg) | TEHA | — | — | TEHA | — | — | TEHA | — | — |
| | 5 | — | — | 5 | — | — | 5 | — | — |
| Oxygen concentration | 7 vol % | 1 vol % | 21 vol % | 0.8 vol % | 10 vol % | 21 vol % | 5 vol % | 0.1 vol % | 21 vol % |
| Number of days of storage | 180 days | 180 days | 180 days | 180 days | 180 days | 180 days | 180 days | 180 days | 180 days |
| Visual observation | No change | No change | No change | No change | No change | No change | No change | No change | No change |
| Result of GC analysis | No change | No change | No change | No change | No change | No change | No change | No change | No change |
| Result of GPC analysis | No polymer formed | No polymer formed | No polymer formed | No polymer formed | No polymer formed | No polymer formed | No polymer formed | No polymer formed | No polymer formed |
| Result of RQ assay | Not detected | Not detected | Not detected | Not detected | Not detected | Not detected | Not detected | Not detected | Not detected |

TABLE 8

| | Example | | | | | |
|---|---|---|---|---|---|---|
| | 65 | 66 | 67 | 68 | 69 | 70 |
| Vinyl ether group-containing (meth) acrylic ester (g) | VEEM | VEEM | VEEM | VEEM | VBA | VBA |
| | 100 | 100 | 100 | 100 | 100 | 100 |
| Radical polymerization inhibitor (mg) | MEHQ | MEHQ | MEHQ | MEHQ | MEHQ | MEHQ |
| | 5 | 10 | 10 | 10 | 5 | 10 |
| Basic compound (mg) | TEHA | — | — | — | TEHA | — |
| | 5 | — | — | — | 5 | — |
| Oxygen concentration | 0.5 vol % | 9 vol % | 21 vol % | 30 vol % | 15 vol % | 0.2 vol % |
| Number of days of storage | 180 days | 180 days | 180 days | 180 days | 180 days | 180 days |
| Visual observation | No change | No change | No change | No change | No change | No change |
| Result of GC analysis | No change | No change | No change | No change | No change | No change |

TABLE 8-continued

| | | | | | | |
|---|---|---|---|---|---|---|
| Result of GPC analysis | No polymer formed | No polymer formed | No polymer formed | No polymer formed | No polymer formed | No polymer formed |
| Result of RQ assay | Not detected | Not detected | Not detected | 10 ppm | Not detected | Not detected |

| | | Example | | | |
|---|---|---|---|---|---|
| | | 71 | 72 | 73 | 74 |
| Vinyl ether group-containing (meth) acrylic ester | | VBA | VBM | VBM | VBM |
| (g) | | 100 | 100 | 100 | 100 |
| Radical polymerization inhibitor | | MEHQ | MEHQ | MEHQ | MEHQ |
| (mg) | | 10 | 5 | 10 | 10 |
| Basic compound | | — | TEHA | — | — |
| (mg) | | — | 5 | — | — |
| Oxygen concentration | | 21 vol % | 18 vol % | 0.3 vol % | 21 vol % |
| Number of days of storage | | 180 days | 180 days | 180 days | 180 days |
| Visual observation | | No change | No change | No change | No change |
| Result of GC analysis | | No change | No change | No change | No change |
| Result of GPC analysis | | No polymer formed | No polymer formed | No polymer formed | No polymer formed |
| Result of RQ assay | | Not detected | Not detected | Not detected | Not detected |

Example 75

The same procedure as in Example 56 was followed except that a 200-mL glass container coated with an opaque tetrafluoroethylene resin on 85% of the inside surface area thereof was used as a structure.

Upon GC, GPC and RQ assay, no deterioration in quality was observed, namely no impurity formation, no high-molecular substance formation or no peroxide formation was detected.

Comparative Example 11

The same procedure as in Example 56 was followed except that a 200-mL transparent glass container was used as a structure.

As a result of visual observation, GC, GPC and RQ assay, impurity formation, the formation of a high-molecular substance with a molecular weight (number average) of 1,500 and peroxide formation (12 ppm) were found.

Reference Example 1

The same procedure as in Comparative Example 11 was followed except that 2-vinyloxyethyl propionate, which is the acryloyl group-free vinyl ether having similar structure as 2-vinyloxyethyl acrylate, was used in lieu of 2-vinyloxyethyl acrylate.

Reference Example 2

The same procedure as in Comparative Example 11 was followed except that 2-ethoxyethyl acrylate, which is the vinyl ether group-free acrylate ester having similar structure as 2-vinyloxyethyl acrylate, was used in lieu of 2-vinyloxyethyl acrylate.

In Reference Examples 1 and 2, each composition in the container after 180 days of storage was evaluated by visual observation, GC, GPC and RQ assay. No deterioration in quality was observed, namely neither impurity formation nor high-molecular substance formation nor peroxide formation was detected.

According to the above results, it can be recognized that the vinyl ether group-containing (meth)acrylic esters have specific properties, which are not seen in either acryloyl group-free vinyl ethers having similar structure or vinyl ether group-free acrylate esters having similar structure.

Example 76

A glass-made 3-liter five-necked flask equipped with a stirrer, thermometer, Oldershaw rectifying column, gas inlet tube and liquid addition line was charged with 529 g of 2-hydroxyethyl vinyl ether containing 11 g of ethylene glycol divinyl ether, 1,502 g of ethyl acrylate, 300 mg of phenothiazine and 10 g of dioctyltinoxide. The contents were mixed and stirred while introducing air into the liquid phase from the gas inlet tube, and heating was started on an oil bath maintained at 130° C. This was the production starting point. The reaction was continued while continuously adding that amount of the acrylate ester corresponding to the weight of ethyl acrylate found in the ethyl acrylate-ethanol azeotrope, namely the distillate at the top of the Oldershaw rectifying column, to the reaction system through the liquid addition line. Samples were taken from the reaction system at 30-minute intervals from the production different catalysts were used. The materials used, the amounts thereof, the reaction time, the product and the yield thereof as determined by GC for each run are shown in Table 9. In cases where methyl methacrylate was used as one of the starting materials, that weight of methyl methacrylate corresponding to the methyl methacrylate in the methyl methacrylate-methanol azeotrope distillate was continuously added to reaction system through the liquid addition line.

TABLE 9

| | Example | | | | | | | | | |
|---|---|---|---|---|---|---|---|---|---|---|
| | 76 | 77 | 78 | 79 | 80 | 81 | 82 | 83 | 84 | 85 |
| (Meth) acrylic ester | AE | AE | AE | MMA | MMA | MMA | AE | AE | MMA | MMA |
| Amount charged (g) | 1502 | 1502 | 1502 | 1502 | 1502 | 1502 | 1502 | 1502 | 1502 | 1502 |
| OH-containing vinyl ether | HEV | HEV | HEV | HEV | HEV | HEV | DEGV | DEGV | DEGV | DEGV |
| Amount charged (g) | 529 | 529 | 529 | 529 | 529 | 529 | 793 | 793 | 793 | 793 |
| Impurity of formula (4) | EGDV | — | EGDV | EGDV | — | EGDV | DEGDV | DEGDV | DEGDV | — |
| Content (g) | 11 | | 11 | 11 | | 11 | 16 | 16 | 16 | |
| Impurity of formula (5) | — | MDOL | MDOL | — | MDOL | MDOL | — | MTOC | — | MTOC |
| Content (g) | | 11 | 8 | | 11 | 8 | | 10 | | 10 |
| Impurity of formula (6) | — | — | — | — | — | — | — | — | — | — |
| Content (g) | | | | | | | | | | |
| Radical polymerization inhibitor | PTZ | PTZ | PTZ | PTZ | PTZ | PTZ | MEHQ | MEHQ | MEHQ | MEHQ |
| Amount added (mg) | 300 | 300 | 300 | 300 | 300 | 300 | 100 | 300 | 100 | 100 |
| Radical polymerization inhibitor | — | — | — | — | — | — | TEMPOL | — | TEMPOL | PTZ |
| Amount added (mg) | | | | | | | 20 | | 20 | 200 |
| Catalyst | DOTO | DOTO | DOTO | DOTO | DOTO | DOTO | DBTO | DBTO | DBTO | DBTO |
| Amount added (mg) | 10 | 10 | 10 | 10 | 10 | 10 | 8 | 8 | 8 | 8 |
| Reaction time (hr) | 8 | 8 | 7.5 | 8 | 8 | 7.5 | 8 | 7.5 | 8 | 8 |
| Product | VEA | VEA | VEA | VEM | VEM | VEM | VEEA | VEEA | VEEM | VEEM |
| Yield (mol %) | 95 | 95 | 95 | 96 | 96 | 96 | 93 | 93 | 95 | 95 |

| | Example | | | | | | | | | |
|---|---|---|---|---|---|---|---|---|---|---|
| | 86 | 87 | 88 | 89 | 90 | 91 | 92 | 93 | 94 | 95 |
| (Meth) acrylic ester | MMA | MMA | MMA | MMA | AE | AE | AE | MMA | MMA | MMA |
| Amount charged (g) | 1502 | 1502 | 1502 | 1502 | 1502 | 1502 | 1502 | 1502 | 1502 | 1502 |
| OH-containing vinyl ether | DEGV | DEGV | DEGV | DEGV | BDV | BDV | BDV | BDV | BDV | BDV |
| Amount charged (g) | 793 | 793 | 793 | 793 | 697 | 697 | 697 | 697 | 697 | 697 |
| Impurity of formula (4) | DEGDV | DEGDV | DEGDV | DEGDV | BDDV | — | — | BDDV | BDDV | — |
| Content (g) | 16 | 16 | 16 | 16 | 14 | | | 14 | 14 | |
| Impurity of formula (5) | — | — | — | — | — | MDOP | — | — | MDOP | — |
| Content (g) | | | | | | 12 | | | 11 | |
| Impurity of formula (6) | — | — | — | — | — | — | 4BVE | — | — | 4BVE |
| Content (g) | | | | | | | 16 | | | 16 |
| Radical polymerization inhibitor | MEHQ | MEHQ | MEHQ | MEHQ | MEHQ | MEHQ | MEHQ | MEHQ | MEHQ | MEHQ |
| Amount added (mg) | 100 | 300 | 100 | 20 | 200 | 200 | 200 | 200 | 200 | 200 |
| Radical polymerization inhibitor | TEMPOL | — | TEMPOL | TEMPOL | TEMPO | TEMPO | TEMPO | TEMPO | TEMPO | TEMPO |
| Amount added (mg) | 20 | | 20 | 50 | 100 | 100 | 100 | 100 | 100 | 100 |
| Catalyst | TBT | DBTOAc | BDBTLO | ZrAA | DBTO | DBTO | DBTO | DBTO | DBTO | DBTO |
| Amount added (mg) | 5 | 10 | 10 | 5 | 8 | 8 | 8 | 8 | 8 | 8 |
| Reaction time (hr) | 8.5 | 8 | 8 | 5.5 | 8 | 8 | 8 | 8 | 7.5 | 8 |
| Product | VEEM | VEEM | VEEM | VEEM | VBA | VBA | VBA | VBM | VBM | VBM |
| Yield (mol %) | 94 | 92 | 93 | 99 | 94 | 94 | 94 | 95 | 95 | 95 | starting point and the yield of the desired 2-vinyloxyethyl acrylate was followed by GC. The yield became constant after 8 hours. The production time was thus 8 hours. The yield of 2-vinyloxyethyl acrylate at that time was 95 mole percent.

Examples 77 to 95

The same procedure as in Example 76 was repeated except that different starting materials, different impurities contained therein, different polymerization inhibitors and The symbols used in Table 9 are as follows.

As regards the (meth)acrylic ester, AE stands for ethyl acrylate, and MMA for methyl methacrylate. As regards the hydroxyl group-containing vinyl ether, HEV stands for 2-hydroxyethyl vinyl ether, DEGV for diethylene glycol monovinyl ether, and BDV for 1,4-butanediol monovinyl ether. As regards the impurity of the general formula (4), namely the compound represented by the general formula (4) given hereinabove, EGDV stands for ethylene glycol divinyl ether, DEGDV for diethylene glycol divinyl ether, and BDDV for 1,4-butanediol divinyl ether. As regards the impurity of the general formula (5), namely the compound represented by the general formula (5) given herein above, MDOL stands for 2-methyl-1,3-dioxolane, MTOC for 2-methyl-1,3,6-trioxocane, and MDOP for 2-methyl-1,3-dioxepane. As regards the impurity of the general formula (6), namely the compound represented by the general formula (6) given herein above, 4BVE stands for 4-butenyl vinyl ether. As for the radical polymerization inhibitor, TEMPOL stands for 4-hydroxy-2,2,6,6-tetramethyl-piperidine-N-oxyl. As regards the catalyst, DBTO stands for dibutyltin oxide, DOTO for dioctyltin oxide, TBT for tetrabutoxytitanium, DBTDAc for dibutyltindiacetate, BDBTLO for bis(dibutyltinlaurtae) oxide, and ZrAA for zirconia acetylacetonate. The other symbols are the same as in Table 1.

vinyl ether used was free of any impurity. The starting materials, polymerization inhibitor and catalyst used, the amounts thereof, the production time found, the product and the yield thereof as determined by GC in each run are shown in Table 10. The symbols used in Table 10 are the same as in Table 9.

TABLE 10

| | Comparative Example | | | | | |
|---|---|---|---|---|---|---|
| | 12 | 13 | 14 | 15 | 16 | 17 |
| (Meth) acrylic ester | AE | MMA | AE | MMA | AE | MMA |
| Amount charged (g) | 1502 | 1502 | 1502 | 1502 | 1502 | 1502 |
| OH-containing vinyl ether | HEV | HEV | DEGV | DEGV | BDV | BDV |
| Amount charged (g) | 529 | 529 | 793 | 793 | 697 | 697 |
| Impurity of formula (4) Content (g) | — | — | — | — | — | — |
| Impurity of formula (5) Content (g) | — | — | — | — | — | — |
| Impurity of formula (6) Content (g) | — | — | — | — | — | — |
| Radical polymerization inhibitor | PTZ | PTZ | MEHQ | MEHQ | MEHQ | MEHQ |
| Amount added (mg) | 300 | 300 | 100 | 100 | 200 | 200 |
| Radical polymerization inhibitor | — | — | TEMPOL | TEMPOL | TEMPO | TEMPO |
| Amount added (mg) | | | 20 | 20 | 100 | 100 |
| Catalyst | DOTO | DOTO | DBTO | DBTO | DBTO | DBTO |
| Amount added (mg) | 10 | 10 | 8 | 8 | 8 | 8 |
| Reaction time (hr) | 12 | 11 | 13 | 12 | 12 | 13 |
| Product | VEA | VEM | VEEA | VEEM | VBA | VBM |
| Yield (mol %) | 95 | 96 | 93 | 95 | 94 | 95 |

Example 96

The same apparatus as used in Example 76 was charged with 529 g of 2-hydroxyethyl vinyl ether, 1,502 g of ethyl acrylate, 300 mg of phenothiazine, 10 g of dioctyltin oxide and 11 g of ethylene glycol divinyl ether, and the same procedure as in Example 76 was carried out. As a result of following by GC, the production time was found to be 8 hours, after which the yield of 2-vinyloxyethyl acrylate was 95 mole percent.

Example 97

The same apparatus as used in Example 76 was charged with 529 g of 2-hydroxyethyl vinyl ether, 1,502 g of ethyl acrylate, 300 mg of phenothiazine and 10 g of dioctyltin oxide, and the reaction was started, with stirring, by immersing the apparatus in an oil bath at 130° C. The same procedure as in Example 76 was followed except that 11 g of ethylene glycol divinyl ether was added 2 hours after the start. As a result of following by GC, the production time was found to be 9 hours, after which the yield of 2-vinyloxyethyl acrylate was 95 mole percent.

Comparative Examples 12 to 17

The same procedure as in Examples 76, 79, 82, 84, 90 or 93 was repeated except that the hydroxyl group-containing

Example 98

A glass-made 3-liter five-necked flask was charged with a stirrer, thermometer, Oldershaw rectifying column, gas inlet tube and liquid addition line was charged with 529 g of 2-hydroxyethyl vinyl ether, 1,502 g of ethyl acrylate, 300 mg of phenothiazine and 10 g of dibutyltin oxide.

On that occasion, the water content of the whole system as determined by the moisture meter was 0.1% by weight. While introducing air into the liquid phase from the gas inlet tube, the contents were mixed and stirred and then temperature raising was started by immersing the flask in an oil bath at 130° C. While continuously adding that amount of the acrylate ester corresponding to the weight of ethyl acrylate in the ethyl acrylate-ethanol azeotrope distilling from the top of the Oldershaw rectifying column to the reaction system through the liquid addition line, the reaction was continued for 12 hours.

As a result of analysis by GC, the yield of the desired 2-vinyloxyethyl acrylate was found to be 95 mole percent. When 10 g of the reaction system was added to 100 mL of hexane, the system was dissolved to give a colorless transparent homogeneous solution.

Examples 99 to 108

The starting materials, polymerization inhibitor, basic compound and catalyst used, the amounts thereof, the water content of the whole system as determine by using the moisture meter, the product and the yield thereof, and the result of the test for solubility in hexane are shown in Table 11 for each run. The symbols used in Table 11 are the same as in Tables 1 to 10. In cases where methyl methacrylate was used as one of the starting materials, that weight of methyl methacrylate corresponding to the methyl methacrylate in the methyl methacrylate-methanol azeotrope distillate was continuously added to reaction system through the liquid addition line.

2-hydroxyethyl vinyl ether, 1,502 g of ethyl acrylate, 300 mg of phenothiazine and 10 g of dibutyltin oxide. The contents were mixed and stirred while introducing an 8% (by vol-

TABLE 11

| | Example | | | | | | | | | | |
|---|---|---|---|---|---|---|---|---|---|---|---|
| | 98 | 99 | 100 | 101 | 102 | 103 | 104 | 105 | 106 | 107 | 108 |
| (Meth) acrylic ester | AE | MMA | AE | MMA | MMA | MMA | MMA | MMA | MMA | AE | MMA |
| Amount charged (g) | 1502 | 1502 | 1502 | 1502 | 1502 | 1502 | 1502 | 1502 | 1502 | 1502 | 1502 |
| OH-containing vinyl ether | HEV | HEV | DEGV | DEGV | DEGV | DEGV | DEGV | DEGV | DEGV | BDV | BDV |
| Amount charged (g) | 529 | 529 | 793 | 793 | 793 | 793 | 793 | 793 | 793 | 697 | 697 |
| Radical polymerization inhibitor | PTZ | PTZ | MEHQ | MEHQ | MEHQ | MEHQ | MEHQ | MEHQ | MEHQ | MEHQ | MEHQ |
| Amount added (mg) | 300 | 300 | 300 | 300 | 300 | 300 | 300 | 300 | 300 | 300 | 300 |
| Basic compound | — | — | — | — | NaOH | — | — | — | — | — | — |
| Amount added (mg) | | | | | 100 | | | | | | |
| Catalyst | DBTO | DBTO | DBTO | DBTO | DBTO | TBT | DBTDAc | BDBTLO | ZrAA | DBTO | DBTO |
| Amount added (mg) | 10 | 10 | 10 | 10 | 10 | 10 | 10 | 10 | 10 | 10 | 10 |
| Water content (wt %) | 0.1 | 0.1 | 0.3 | 0.1 | 0.1 | 0.1 | 0.1 | 0.1 | 0.1 | 0.1 | 0.1 |
| Product | VEA | VEM | VEEA | VEEM | VEEM | VEEM | VEEM | VEEM | VEEM | VBA | VBM |
| Yield (mol %) | 95 | 96 | 93 | 95 | 95 | 94 | 92 | 93 | 99 | 94 | 95 |
| Solubility in hexane | Colorless, clear | Colorless, clear | Colorless, clear | Colorless, clear | Colorless, clear | Colorless, clear | Colorless, clear | Colorless, clear | Colorless, clear | Colorless, clear | Colorless clear |

Comparative Examples 18 to 23

The starting materials, polymerization inhibitor, basic compound and catalyst used, the amounts thereof, the water content of the whole system as determine by using the moisture meter, the product and the yield thereof, and the result of the test for solubility in hexane are shown in Table 12 for each run. The symbols used in Table 12 are the same as in Tables 1 to 10.

ume) oxygen gas (the balance being nitrogen) into the liquid phase from the gas inlet tube, and heating was started on an oil bath maintained at 130° C. The reaction was continued for 12 hours while continuously adding that amount of the ethyl acrylate corresponding to the weight of the ethyl acrylate found in the ethyl acrylate-ethanol azeotrope, namely the distillate at the top of the Oldershaw rectifying column, to the reaction system through the liquid addition line. The molecular oxygen concentration in the gaseous

TABLE 12

| | Comparative Example | | | | | |
|---|---|---|---|---|---|---|
| | 18 | 19 | 20 | 21 | 22 | 23 |
| (Meth) acrylic ester | AE | MMA | AE | MMA | AE | MMA |
| Amount charged (g) | 1502 | 1502 | 1502 | 1502 | 1502 | 1502 |
| OH-containing vinyl ether | HEV | HEV | DEGV | DEGV | DEGV | DEGV |
| Amount charged (g) | 529 | 529 | 793 | 793 | 793 | 793 |
| Radical polymerization inhibitor | PTZ | PTZ | MEHQ | MEHQ | MEHQ | MEHQ |
| Amount added (mg) | 300 | 300 | 300 | 300 | 300 | 300 |
| Catalyst | DBTO | DBTO | DBTO | DBTO | DBTO | TBT |
| Amount added (mg) | 10 | 10 | 10 | 10 | 10 | 10 |
| Water content (wt %) | 6.0 | 6.0 | 6.0 | 6.0 | 5.5 | 5.5 |
| Product | VEA | VEM | VEEA | VEEM | VEEM | VEEM |
| Yield (mol %) | 93 | 94 | 89 | 91 | 92 | 90 |
| Solubility in hexane | Slightly turbid | Slightly turbid | Slightly turbid | Slightly turbid | Slightly turbid | Slightly turbid |

Example 109

A glass-made 3-liter five-necked flask equipped with a stirrer, thermometer, Oldershaw rectifying column, gas inlet tube and liquid addition line was charged with 529 g of phase during reaction was 0.1 to 8% by volume. As a result of analysis by GC, the yield of the desired 2-vinyloxyethyl acrylate was found to be 96 mole percent. No solid matter formation was found either in the gaseous phase or in the liquid phase of the reaction system. As a result of analysis of the liquid phase by RQ assay, no peroxide was detected.

Example 110

The same procedure as in Example 109 was followed except that a 8% (by volume) oxygen gas (the balance being nitrogen) was introduced into the gaseous phase. The molecular oxygen concentration in the gaseous phase during reaction was 0.1 to 8% by volume.

As a result of analysis by GC, the yield of the desired 2-vinyloxyethyl acrylate was found to be 96 mole percent. No solid matter formation was found either in the gaseous phase or in the liquid phase of the reaction system. As a result of analysis of the liquid phase by RQ assay, no peroxide was detected.

Examples 111 to 116

The same procedure as in Example 109 was repeated except that the (meth)acrylic ester and/or hydroxyl group-containing vinyl ether and/or radical polymerization inhibitor used differed in species and/or the amounts thereof were varied and that the oxygen concentration was varied and further that a basic compound was used or not used. The species used, the amounts thereof, the vinyl ether group-containing (meth)acrylic ester produced and the yield thereof, the molecular oxygen concentration in the gaseous phase during reaction, and the absence or presence of a solid matter in the gaseous phase and in the liquid phase of the reaction system and the result of analysis by RQ assay are shown for each run in Table 13. The symbols used in Table 13 are the same as in Tables 1 to 12.

In cases where methyl methacrylate was used as one of the starting materials, that weight of methyl methacrylate corresponding to the methyl methacrylate in the methyl methacrylate-methanol azeotrope distillate was continuously added to reaction system through the liquid addition line.

130° C., and the temperature was allowed to begin to rise. The reaction was continued for 12 hours while continuously adding that amount of ethyl acrylate corresponding to the weight of the ethyl acrylate found in the ethyl acrylate-ethanol azeotrope, namely the distillate at the top of the Oldershaw rectifying column, to the reaction system through the liquid addition line. As a result of analysis by GC, the yield of the desired 2-(vinyloxyethoxy) ethyl acrylate was found to be 95 mole percent. No solid matter formation was found either in the gaseous phase or in the liquid phase of the reaction system.

Example 118

The same procedure as in Example 117 was followed except that 1,502 g of methyl methacrylate was used in lieu of ethyl acrylate.

As a result of analysis by GC, the yield of the desired 2-(vinyloxyethoxy) ethyl methacrylate was found to be 97 mole percent. No solid matter formation was found either in the gaseous phase or in the liquid phase of the reaction system.

Example 119

A glass-made 3-liter five-necked flask equipped with a stirrer, thermometer, Oldershaw rectifying column, gas inlet tube and liquid addition line was charged with 793 g of diethylene glycol monovinyl ether, 1,502 g of ethyl acrylate, 300 mg of phenothiazine and 10 g of dioctyltin oxide. The contents were mixed and stirred while introducing an 8% (by volume) nitrogen monoxide gas (the balance being nitrogen) into the liquid phase from the gas inlet tube, and heating was started on an oil bath maintained at 130° C. The reaction was continued for 12 hours while continuously

TABLE 13

|  | Example | | | | | |
| --- | --- | --- | --- | --- | --- | --- |
|  | 111 | 112 | 113 | 114 | 115 | 116 |
| (Meth) acrylic ester | AE | MMA | AE | MMA | AE | MMA |
| Amount charged (g) | 1502 | 1502 | 1502 | 1502 | 1502 | 1502 |
| OH-containing vinyl ether | HEV | HEV | DEGV | DEGV | BDV | BDV |
| Amount charged (g) | 529 | 529 | 793 | 793 | 697 | 697 |
| Radical polymerization inhibitor | PTZ | MEHQ | PTZ | MEHQ | PTZ | MEHQ |
| Amount added (mg) | 300 | 300 | 300 | 300 | 300 | 300 |
| Basic compound | NaOH | — | NaOH | — | NaOH | — |
| Amount added (mg) | 100 | | 100 | | 100 | |
| Catalyst | DBTO | DBTO | DBTO | DBTO | DBTO | DBTO |
| Amount added (mg) | 10 | 10 | 10 | 10 | 10 | 10 |
| Oxygen concentration (vol %) | 6 | 10 | 2 | 0.5 | 5 | 7 |
| Molecular oxygen concentration in gaseous phase during reaction (vol %) | 0.05~6 | 0.1~10 | 0.03~2 | 0.02~0.5 | 0.08~5 | 0.1~7 |
| Product | VEA | VEM | VEEA | VEEM | VBA | VBM |
| Yield (mol %) | 96 | 97 | 93 | 95 | 94 | 95 |
| Solid matter formation in liquid phase | No | No | No | No | No | No |
| Solid matter formation in gaseous phase | No | No | No | No | No | No |
| Result of RQ assay | Not detected | Not detected | Not detected | Not detected | Not detected | Not detected |

A glass-made 3-liter five-necked flask equipped with a stirrer, thermometer, Oldershaw rectifying column and liquid addition line was charged with 793 g of diethylene glycol monovinyl ether, 1,502 g of ethyl acrylate, 300 mg of phenothiazine, 300 mg of Aluminum N-nitrosophenylhydroxylamine and 10 g of dioctyltin oxide. While mixing and stirring, the flask was immersed in an oil bath maintained at adding that amount of ethyl acrylate corresponding to the weight of the ethyl acrylate found in the ethyl acrylate-ethanol azeotrope, namely the distillate at the top of the Oldershaw rectifying column, to the reaction system through the liquid addition line.

The nitrogen monoxide concentration in the gaseous phase during reaction was 0.1 to 8% by volume.

As a result of analysis by GC, the yield of the desired 2-(vinyloxyethoxy) ethyl acrylate was found to be 96 mole percent. No solid matter formation was found either in the gaseous phase or in the liquid phase of the reaction system.

Example 120

The same procedure as in Example 109 was followed except that an 8% (by volume) nitrogen monoxide gas (the balance being nitrogen) was introduced into the gaseous phase. The molecular nitrogen monooxide concentration in the gaseous phase during reaction was 0.1 to 8% by volume.

As a result of analysis by GC, the yield of the desired 2-(vinyloxyethoxy) ethyl acrylate was found to be 96 mole percent. No solid matter formation was found either in the gaseous phase or in the liquid phase of the reaction system.

Example 121

The same procedure as in Example 119 was followed except that 1,502 g of methyl methacrylate was used in lieu of ethyl acrylate. The molecular nitrogen monooxide concentration in the gaseous phase during reaction was 0.1 to 8% by volume.

As a result of analysis by GC, the yield of the desired 2-(vinyloxyethoxy) ethyl methacrylate was found to be 97 mole percent. No solid matter formation was found either in the gaseous phase or in the liquid phase of the reaction system.

Comparative Example 24

The same procedure as in Example 109 was followed without introducing the 8% (by volume) oxygen gas (the balance being nitrogen). After 2 hours, a white solid was formed in the gaseous phase and liquid phase and, therefore, the reaction was discontinued.

Example 122

A lightproof structure, namely a 3-liter separable apparatus made of SUS 316and equipped with a stirrer, thermometer holder, gas inlet tube, liquid addition line and rectifying column was charged with 529 g of 2-hydroxyethyl vinyl ether, 1,502 g of ethyl acrylate, 300 mg of phenothiazine and 10 g of dibutyltin oxide. The contents were mixed and stirred while introducing air into the liquid phase from the gas inlet tube, and heating was started on an oil bath maintained at 130° C. The reaction was continued for 12 hours while continuously adding that amount of ethyl acrylate corresponding to the weight of the ethyl acrylate found in the ethyl acrylate-ethanol azeotrope, namely the distillate at the top of the Oldershaw rectifying column, to the reaction system through the liquid addition line.

The molecular oxygen concentration in the gaseous phase during reaction was 0.1 to 21% by volume.

As a result of analysis by GC, the yield of the desired 2-vinyloxyethyl acrylate was found to be 96 mole percent. No solid matter formation was found either in the gaseous phase or in the liquid phase of the reaction system. As a result of analysis of the liquid phase by RQ assay, 3 ppm of peroxide was detected.

Example 123

The same procedure as in Example 122 was followed except that a 15% (by volume) oxygen gas (the balance being nitrogen) was introduced in lieu of air. The molecular oxygen concentration in the gaseous phase during reaction was 0.1 to 15% by volume.

As a result of analysis by GC, the yield of the desired 2-vinyloxyethyl acrylate was found to be 96 mole percent. No solid matter formation was found either in the gaseous phase or in the liquid phase of the reaction system. As a result of analysis by RQ assay, no peroxide was detected.

Examples 124 to 131

The same procedure as in Example 123 was repeated except that the (meth)acrylic ester and/or hydroxyl group-containing vinyl ether and/or radical polymerization inhibitor used differed in species and/or the amounts thereof were varied and that the oxygen concentration was varied and further that a basic compound was used or not used. The species used, the amounts thereof, the vinyl ether group-containing (meth)acrylic ester produced and the yield thereof, the molecular oxygen concentration in the gaseous phase during reaction, and the absence or presence of a solid matter in the gaseous phase and in the liquid phase of the reaction system and the result of analysis by RQ assay are shown for each run in Table 14. The symbols used in Table 14 are the same as in Tables 1 to 13.

In cases where methyl methacrylate was used as one of the starting materials, that weight of methyl methacrylate corresponding to the methyl methacrylate in the methyl methacrylate-methanol azeotrope distillate was continuously added to reaction system through the liquid addition line.

TABLE 14

| | Example | | | | | | | |
|---|---|---|---|---|---|---|---|---|
| | 124 | 125 | 126 | 127 | 128 | 129 | 130 | 131 |
| (Meth) acrylic ester | AE | MMA | AE | AE | MMA | MMA | AE | MMA |
| Amount charged (g) | 1502 | 1502 | 1502 | 1502 | 1502 | 1502 | 1502 | 1502 |
| OH-containing vinyl ether | HEV | HEV | DEGV | DEGV | DEGV | DEGV | BDV | BDV |
| Amount charged (g) | 529 | 529 | 793 | 793 | 793 | 793 | 697 | 697 |
| Radical polymerization inhibitor | MEHQ | PTZ | TEMPO | MEHQ | PTZ | MEHQ | MEHQ | TEMPO |
| Amount added (mg) | 200 | 300 | 300 | 250 | 300 | 200 | 300 | 300 |
| Basic compound | TEHA | — | — | NaOH | — | TEHA | NaOH | — |
| Amount added (mg) | 100 | | | 100 | | 100 | 80 | |
| Catalyst | DBTO | DBTO | DBTO | DBTO | DBTO | DBTO | DBTO | DBTO |
| Amount added (mg) | 10 | 10 | 10 | 10 | 10 | 10 | 10 | 10 |
| Oxygen concentration (vol %) | 7 | 10 | 8 | 5 | 0.5 | 0.2 | 1 | 2 |

TABLE 14-continued

| | Example | | | | | | | |
|---|---|---|---|---|---|---|---|---|
| | 124 | 125 | 126 | 127 | 128 | 129 | 130 | 131 |
| Molecular oxygen concentration in gaseous phase during reaction (vol %) | 0.1~7 | 0.1~10 | 0.1~8 | 0.1~5 | 0.1~0.5 | 0.1~0.2 | 0.1~1 | 0.1~2 |
| Product | VEA | VEM | VEEA | VEEA | VEEM | VEEM | VBA | VBM |
| Yield (mol %) | 96 | 97 | 93 | 93 | 95 | 95 | 94 | 95 |
| Solid matter formation in liquid phase | No | No | No | No | No | No | No | No |
| Solid matter formation in gaseous phase | No | No | No | No | No | No | No | No |
| Result of RQ assay | Not detected | Not detected | Not detected | Not detected | Not detected | Not detected | Not detected | Not detected |

Example 132

The same procedure as in Example 123 was followed except that the upper lid-forming portion of the SUS 316-made separable apparatus used in Example 123 was replaced with a transparent glass lid (in this case, the lightproof material SUS 316 accounted for 83% of the reaction apparatus structure inside surface area otherwise through which light could reach within the structure inside). The molecular oxygen concentration in the gaseous phase during reaction was 0.1 to 15% by volume.

As a result of analysis by GC, the yield of the desired 2-vinyloxyethyl acrylate was found to be 96 mole percent. No solid matter formation was found either in the gaseous phase or in the liquid phase of the reaction system. As a result of analysis by RQ assay, no peroxide was detected.

Comparative Example 25

The same procedure as in Example 109 was followed except that air was introduced in lieu of the 8% (by weight) oxygen gas (the balance being nitrogen). The molecular oxygen concentration in the gaseous phase during reaction was 0.1 to 21% by volume.

As a result of analysis by GC, the yield of the desired 2-vinyloxyethyl acrylate was found to be 96 mole percent. No solid matter formation was found either in the gaseous phase or in the liquid phase of the reaction system. As a result of analysis by RQ assay, however, 17 ppm of peroxide was detected.

Comparative Example 26

The same procedure as in Example 109 was followed except that a 15% (by volume) oxygen gas (the balance being nitrogen) was introduced in lieu of the 8% (by weight) oxygen gas (the balance being nitrogen). The molecular oxygen concentration in the gaseous phase during reaction was 0.1 to 15% by volume.

As a result of analysis by GC, the yield of the desired 2-vinyloxyethyl acrylate was found to be 96 mole percent. No solid matter formation was found either in the gaseous phase or in the liquid phase of the reaction system. As a result of analysis by RQ assay, however, 12 ppm of peroxide was detected.

Example 133

Raw Material Recovery Procedure

The reaction mixture obtained by the same procedure as in Example 127 was introduced into a glass-made 3-liter distillation apparatus equipped with a stirrer, thermometer holder, gas inlet tube, pressure reducing regulator and rectifying column. While introducing an 8% (by volume) oxygen gas (the balance being nitrogen) into the liquid phase, the contents were mixed and stirred and heating was started on an oil bath maintained at 130° C. By reducing the pressure gradually from 667 hPa to 67 hPa, ethyl acrylate and ethanol were allowed to distill out of the top of the rectifying column and the starting material ethyl acrylate was recovered. The molecular oxygen concentration in the gaseous phase during raw material recovery procedure was 0.1 to 8% by volume.

No solid matter formation was observed either in the gaseous phase or in the liquid phase of the distillation apparatus. Furthermore, as a result of analysis of the liquid phase by RQ assay, no peroxide was detected.

Example 134

Raw Material Recovery Procedure

The same procedure as in Example 133 was followed except that a 10% (by volume) oxygen gas (the balance being nitrogen) was introduced in lieu of the 8% (by volume) oxygen gas (the balance being nitrogen). The molecular oxygen concentration in the gaseous phase during raw material recovery procedure was 0.1 to 10% by volume.

No solid matter formation was observed either in the gaseous phase or in the liquid phase of the distillation apparatus. Furthermore, as a result of analysis of the liquid phase by RQ assay, no peroxide was detected.

Example 135

Raw Material Recovery Procedure

The same procedure as in Example 133 was followed except that a 0.1% (by volume) oxygen gas (the balance being nitrogen) was introduced in lieu of the 8% (by volume) oxygen gas (the balance being nitrogen). The molecular oxygen concentration in the gaseous phase during raw material recovery procedure was 0.02 to 0.1% by volume.

No solid matter formation was observed either in the gaseous phase or in the liquid phase of the distillation apparatus. Furthermore, as a result of analysis of the liquid phase by RQ assay, no peroxide was detected.

Example 136

Raw Material Recovery Procedure

The same procedure as in Example 133 was followed except that the reaction mixture obtained by the same procedure as in Example 129 was introduced in lieu of the reaction mixture obtained by the same procedure as in Example 127. Methyl methacrylate and methanol were thus allowed to distill out of the top of the rectifying column and the starting material methyl methacrylate was recovered. The molecular oxygen concentration in the gaseous phase during raw material recovery procedure was 0.1 to 8% by volume.

No solid matter formation was observed either in the gaseous phase or in the liquid phase of the distillation apparatus. Furthermore, as a result of analysis of the liquid phase by RQ assay, no peroxide was detected.

Example 137

Raw Material Recovery Procedure

Following the procedure of Example 133, the contents in the apparatus were mixed and stirred while introducing an 8% (by volume) oxygen gas (the balance being nitrogen) into the liquid phase, and the temperature was raised on an oil bath at 150° C. By reducing the pressure to 17 hPa, that portion of the starting material diethylene glycol monovinyl ether remaining unreacted was caused to distill off from the top of the rectifying column and thus recovered. The molecular oxygen concentration in the gaseous phase during raw material recovery procedure was 0.1 to 8% by volume.

No solid matter formation was observed either in the gaseous phase or in the liquid phase of the distillation apparatus. Furthermore, as a result of analysis of the liquid phase by RQ assay, no peroxide was detected.

Example 138

Raw Material Recovery Procedure

Following the procedure of Example 136, the same procedure as in Example 137 was followed. The molecular oxygen concentration in the gaseous phase during raw material recovery procedure was 0.1 to 8% by volume.

No solid matter formation was observed either in the gaseous phase or in the liquid phase of the distillation apparatus. Furthermore, as a result of analysis of the liquid phase by RQ assay, no peroxide was detected.

Example 139

Distillation/Purification Procedure

The mixture obtained by the same procedure as in Example 137 was introduced into a glass-made one-liter distillation apparatus equipped with a stirrer, thermometer holder, gas inlet tube, pressure reducing regulator and rectifying column. While introducing an 8% (by volume) oxygen gas (the balance being nitrogen) into the liquid phase from the gas inlet tube, the contents were mixed and stirred and heating was started on an oil bath maintained at 150° C. By reducing the pressure gradually to 13 hPa, 2-(vinyloxyethoxy)ethyl acrylate was caused to distill off from the top of the rectifying column for purifying the same. The molecular oxygen concentration in the gaseous phase during distillation/purification was 0.1 to 8% by volume.

No solid matter formation was observed either in the gaseous phase or in the liquid phase of the distillation apparatus. Furthermore, as a result of analysis by RQ assay of the liquid phase and of the distillate 2-(vinyloxyethoxy) ethyl acrylate, no peroxide was detected.

Example 140

Distillation/Purification Procedure

The same procedure as in Example 139 was followed except that the mixture obtained by the same procedure as in Example 138 was introduced in lieu of the mixture obtained by the same procedure as in Example 137, to thereby causing 2-(vinyloxyethoxy)ethyl methacrylate to distill out for purifying the same. The molecular oxygen concentration in the gaseous phase during distillation/purification was 0.1 to 8% by volume.

No solid matter formation was observed either in the gaseous phase or in the liquid phase of the distillation apparatus. Furthermore, as a result of analysis by RQ assay of the liquid phase and of the distillate 2-(vinyloxyethoxy) ethyl methacrylate, no peroxide was detected.

Example 141

Water Washing Procedure

A 400-mL portion of the reaction mixture obtained by the same procedure as in Example 127 was introduced, together with 400 mL of a 1 N aqueous solution of sodium hydroxide, into a glass-made one-liter separating apparatus equipped with a stirrer and a gas inlet tube. While introducing an 8% (by volume) oxygen gas (the balance being nitrogen) into the gaseous phase from the gas inlet tube, the contents were stirred at room temperature for 1 hour, and then the contents were allowed to stand for 1 hour, whereby they separated into an oil phase, an aqueous phase and a catalyst phase. After removing the aqueous phase containing unreacted diethylene glycol monovinyl ether, the catalyst phase was removed by filtration.

No solid matter formation was observed either in the gaseous phase or in the liquid phase of the separating apparatus. Furthermore, as a result of analysis of the oily phase by RQ assay, no peroxide was detected.

Example 142

Water Washing Procedure

The same procedure as in Example 141 was followed except that the reaction mixture obtained by the same procedure as in Example 129 was introduced in lieu of the reaction mixture obtained by the same procedure as in Example 127, to thereby remove the aqueous phase containing unreacted diethylene glycol monovinyl ether and the catalyst layer.

No solid matter formation was observed either in the gaseous phase or in the liquid phase of the separating apparatus. Furthermore, as a result of analysis of the oil phase by RQ assay, no peroxide was detected.

Example 143

Raw Material Recovery Procedure

The reaction mixture obtained by the same procedure as in Example 127 was introduced into a lightproof structure, namely a SUS 316-made 3-liter distillation apparatus equipped with a stirrer, thermometer holder, gas inlet tube, pressure reduction regulator and rectifying column. While introducing a 15% (by volume) oxygen gas (the balance being nitrogen) into the liquid phase through the gas inlet tube, the contents were mixed and stirred, and heating was started on an oil bath at 130° C. By reducing the pressure gradually from 667 hPa to 67 hPa, ethyl acrylate and ethanol were allowed to distill out of the top of the rectifying column and thus the starting material ethyl acrylate was recovered. The molecular oxygen concentration in the gaseous phase during raw material recovery procedure was 0.1 to 15% by volume.

No solid matter formation was observed either in the gaseous phase or in the liquid phase of the distillation apparatus. Furthermore, as a result of analysis of the liquid phase by RQ assay, no peroxide was detected.

Example 144

Raw Material Recovery Procedure

The same procedure as in Example 143 was followed except that an 8% (by volume) oxygen gas (the balance being nitrogen) was introduced in lieu of the 15% (by volume) oxygen gas (the balance being nitrogen). The molecular oxygen concentration in the gaseous phase during raw material recovery procedure was 0.1 to 8% by volume.

No solid matter formation was observed either in the gaseous phase or in the liquid phase of the distillation apparatus. Furthermore, as a result of analysis of the liquid phase by RQ assay, no peroxide was detected.

Example 145

Raw Material Recovery Procedure

The same procedure as in Example 143 was followed except that a 0.1% (by volume) oxygen gas (the balance being nitrogen) was introduced in lieu of the 15% (by volume) oxygen gas (the balance being nitrogen). The molecular oxygen concentration in the gaseous phase during raw material recovery procedure was 0.02 to 0.1% by volume.

No solid matter formation was observed either in the gaseous phase or in the liquid phase of the distillation apparatus. Furthermore, as a result of analysis of the liquid phase by RQ assay, no peroxide was detected.

Example 146

Raw Material Recovery Procedure

The same procedure as in Example 143 was followed except that the reaction mixture obtained by the same procedure as in Example 129 was introduced in lieu of the reaction mixture obtained by the same procedure as in Example 127, to thereby cause methyl methacrylate and methanol to distill out of the top of the rectifying column for recovering the starting material methyl methacrylate. The molecular oxygen concentration in the gaseous phase during raw material recovery procedure was 0.1 to 15% by volume.

No solid matter formation was observed either in the gaseous phase or in the liquid phase of the distillation apparatus. Furthermore, as a result of analysis of the liquid phase by RQ assay, no peroxide was detected.

Example 147

Raw Material Recovery Procedure

Following the procedure of Example 143, the residue was stirred while introducing a 15% (by volume) oxygen gas (the balance being nitrogen) into the liquid phase, and heating was started on an oil bath at 150° C. By reducing the pressure to 17 hPa, the unreacted portion of the starting material diethylene glycol monovinyl ether was distilled out of the top of the rectifying column for recovering the same. The molecular oxygen concentration in the gaseous phase during raw material recovery procedure was 0.1 to 15% by volume.

No solid matter formation was observed either in the gaseous phase or in the liquid phase of the distillation apparatus. Furthermore, as a result of analysis of the liquid phase by RQ assay, no peroxide was detected.

Example 148

Raw Material Recovery Procedure

Following the procedure of Example 146, the same procedure as in Example 147 was followed. The molecular oxygen concentration in the gaseous phase during raw material recovery procedure was 0.1 to 15% by volume.

No solid matter formation was observed either in the gaseous phase or in the liquid phase of the distillation apparatus. Furthermore, as a result of analysis by RQ assay of the liquid phase, no peroxide was detected.

Comparative Example 27

Raw Material Recovery Procedure

The same procedure as in Example 133 was followed except that a 15% (by volume) oxygen gas (the balance being nitrogen) was introduced in lieu of the 8% (by volume) oxygen gas (the balance being nitrogen). The molecular oxygen concentration in the gaseous phase during raw material recovery procedure was 0.1 to 15% by volume.

No solid matter formation was observed either in the gaseous phase or in the liquid phase of the distillation apparatus. Furthermore, as a result of analysis by RQ assay of the liquid phase, 12 ppm of peroxide was detected.

Example 149

Distillation/Purification Procedure

The mixture obtained by the same procedure as in Example 147 was introduced into a lightproof structure, namely a SUS 316-made one-liter distillation apparatus equipped with a stirrer, thermometer holder, gas inlet tube, pressure reduction regulator and rectifying column. While introducing a 15% (by volume) oxygen gas (the balance being nitrogen) into the liquid phase through the gas inlet tube, the contents were mixed and stirred, and heating was started on an oil bath at 150° C. By reducing the pressure to 13 hPa, 2-(vinyloxyethoxy)ethyl acrylate was allowed to distill out of the top of the rectifying column and the same was thus purified. The molecular oxygen concentration in the gaseous phase during distillation/purification was 0.1 to 15% by volume.

No solid matter formation was observed either in the gaseous phase or in the liquid phase of the distillation apparatus. Furthermore, as a result of analysis by RQ assay of the liquid phase and of the distillate 2-(vinyloxyethoxy) ethyl acrylate, no peroxide was detected.

Example 150

Distillation/Purification Procedure

The same procedure as in Example 149 was followed except that the mixture obtained by the same procedure as in Example 148 was introduced in lieu of the mixture obtained by the same procedure as in Example 147, to thereby cause 2-(vinyloxyethoxy)ethyl methacrylate to distill out for purifying the same. The molecular oxygen concentration in the gaseous phase during distillation/purification was 0.1 to 15% by volume.

No solid matter formation was observed either in the gaseous phase or in the liquid phase of the distillation apparatus. Furthermore, as a result of analysis by RQ assay of the liquid phase and of the distillate 2-(vinyloxyethoxy) ethyl methacrylate, no peroxide was detected.

Comparative Example 28

Distillation/Purification Procedure

The same procedure as in Example 139 was followed except that a 15% (by volume) oxygen gas (the balance being nitrogen) was introduced in lieu of the 8% (by volume) oxygen gas (the balance being nitrogen). The molecular oxygen concentration in the gaseous phase during distillation/purification was 0.1 to 15% by volume.

No solid matter formation was observed either in the gaseous phase or in the liquid phase of the distillation apparatus. Furthermore, as a result of analysis of the liquid phase by RQ assay, 21 ppm of peroxide was detected.

Example 151

Water Washing Procedure

A 400-mL portion of the reaction mixture obtained by the same procedure as in Example 127 was introduced, together with 400 mL of a 1 N aqueous solution of sodium hydroxide, into a lightproof structure, namely a SUS 136-made one-liter separating apparatus equipped with a stirrer and a gas inlet tube. While introducing a 15% (by volume) oxygen gas (the balance being nitrogen) into the gaseous phase, the contents were stirred at room temperature for 1 hour, and then the contents were allowed to stand for 1 hour, whereby they separated into an oil phase, an aqueous phase and a catalyst phase. After removing the aqueous phase containing unreacted diethylene glycol monovinyl ether, the catalyst phase was removed by filtration.

No solid matter formation was observed either in the gaseous phase or in the liquid phase of the separating apparatus. Furthermore, as a result of analysis of the oily phase by RQ assay, no peroxide was detected.

Example 152

Water Washing Procedure

The same procedure as in Example 151 was followed except that the reaction mixture obtained by the same procedure as in Example 129 was introduced in lieu of the reaction mixture obtained by the same procedure as in Example 127, to thereby remove the aqueous phase containing unreacted diethylene glycol monovinyl ether and the catalyst layer.

No solid matter formation was observed either in the gaseous phase or in the liquid phase of the separating apparatus. Furthermore, as a result of analysis of the oily phase by RQ assay, no peroxide was detected.

Comparative Example 29

Water Washing Procedure

The same procedure as in Example 141 was followed except that a 15% (by volume) oxygen gas (the balance being nitrogen) was introduced in lieu of the 8% (by volume) oxygen gas (the balance being nitrogen).

No solid matter formation was observed either in the gaseous phase or in the liquid phase of the separating apparatus. However, as a result of analysis of the oily phase by RQ assay, 10 ppm of peroxide was detected.

The invention claimed is:

1. A method of producing a vinyl ether group-containing (meth) acrylic ester represented by the following formula (1):

$$CH_2=CR^1-COO-R^2-O-CH=CH-R^3 \quad (1)$$
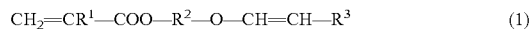

in the formula, $R^1$ represents a hydrogen atom or a methyl group, $R^2$ represents a straight, branched or cyclic alkylene group containing 2 to 20 carbon atoms, an alkylene group containing 2 to 20 carbon atoms and having at least one oxygen atom in the form of an ether linkage and/or an ester linkage within the structure thereof, or an aromatic group which contains 6 to 11 carbon atoms and may optionally be substituted, $R^3$ represents a hydrogen atom, a straight, branched or cyclic alkyl group containing 1 to 10 carbon atoms, or an aromatic group which contains 6 to 11 carbon atoms and may optionally be substituted, and which comprises reacting a hydroxyl group-containing vinyl ether represented by the following formula (2):

$$R^3-CH=CH-O-R^2-OH \quad (2)$$

in the formula, $R^2$ represents a straight, branched or cyclic alkylene group containing 2 to 20 carbon atoms, an alkylene group containing 2 to 20 carbon atoms and having at least one oxygen atom in the form of an ether linkage and/or an ester linkage within the structure thereof, or an aromatic group which contains 6 to 11 carbon atoms and may optionally be substituted, and $R^3$ represents a hydrogen atom, a straight, branched or cyclic alkyl group containing 1 to 10 carbon atoms, or an aromatic group which contains 6 to 11 carbon atoms and may optionally be substituted, with a (meth)acrylic ester represented by the following formula (3):

$$CH_2=CR^1-COOR^4 \quad (3):$$

in the formula, $R^1$ represents a hydrogen atom or a methyl group and $R^4$ represents a straight, branched or cyclic alkyl group containing 1 to 8 carbon atoms and at least one compound selected from the group consisting of a divinyl ether represented by the following formula (4):

$$R^3-CH=CH-O-R^2-O-CH=CH-R^3 \quad (4)$$
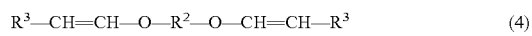

in the formula, $R^2$ represents a straight, branched or cyclic alkylene group containing 2 to 20 carbon atoms, an alkylene group containing 2 to 20 carbon atoms and having at least one oxygen atom in the form of an ether linkage and/or an ester linkage within the structure thereof, or an aromatic group which contains 6 to 11 carbon atoms and may optionally be substituted, and the two $R^3$ groups are the same or different and each represents a hydrogen atom, a straight, branched or cyclic alkyl group containing 1 to 10 carbon atoms, or an aromatic group which contains 6 to 11 carbon atoms and may optionally be substituted, a 2-substituted-1,3-dioxo compound represented by the following formula (5):

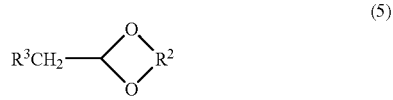

(5)

in the formula, $R^2$ represents a straight, branched or cyclic alkylene group containing 2 to 20 carbon atoms, an alkylene group containing 2 to 20 carbon atoms and having at least one oxygen atom in the form of an ether linkage and/or an ester linkage within the structure thereof, or an aromatic group which contains 6 to 11 carbon atoms and may optionally be substituted, and $R^3$ represents a hydrogen atom, a straight, branched or cyclic alkyl group containing 1 to 10 carbon atoms, or an aromatic group which contains 6 to 11 carbon atoms, and may optionally be substituted, and an unsaturated bond-containing vinyl ether represented by the following formula (6):

 (6)

in the formula, $R^3$ represents a hydrogen atom, a straight, branched or cyclic alkyl group containing 1 to 10 carbon atoms, or an aromatic group which contains 6 to 11 carbon atoms and may optionally be substituted; $R^5$ represents an organic residue containing an unsaturated bond represented by $-CR^6=CR^7$; and $R^6$ and $R^7$ are the same or different and each represents a hydrogen atom or an organic residue.

2. The method of producing a vinyl ether group-containing (meth)acrylic ester according to claim 1, wherein the vinyl ether group-containing (meth)acrylic ester is produced in an atmosphere such that a molecular oxygen concentration is 0.01 to 10% by volume.

3. A method of purifying a vinyl ether group-containing (meth) acrylic ester prepared by the method of producing a vinyl ether group-containing (meth)acrylic ester according to claim 1, which comprises carrying out said method of purifying a vinyl ether group-containing (meth)acrylic ester in an atmosphere such that a molecular oxygen concentration in the gaseous phase in the purification system is 0.01 to 10% by volume, wherein said purification of a vinyl ether group-containing (meth)acrylic esters is carried out in the manner of distillation purification.

* * * * *

UNITED STATES PATENT AND TRADEMARK OFFICE
CERTIFICATE OF CORRECTION

PATENT NO. : 7,321,051 B2  
APPLICATION NO. : 09/982861  
DATED : January 22, 2008  
INVENTOR(S) : Keiji Yurugi and Hiroko Yamaguchi It is certified that error appears in the above-identified patent and that said Letters Patent is hereby corrected as shown below:

In column 54 and 55, please amend claim 1 line 19-25 as follows:

1. A method of producing a vinyl ether group-containing (meth) acrylic ester represented by the following formula (1):

$$CH_2=CR^1\text{-}COO\text{-}R^2\text{-}O\text{-}CH=CH\text{-}R^3 \qquad (1)$$

in the formula, $R^1$ represents a hydrogen atom or a methyl group, $R^2$ represents a straight, branched or cyclic alkylene group containing 2 to 20 carbon atoms, an alkylene group containing 2 to 20 carbon atoms and having at least one oxygen atom in the form of an ether linkage and/or an ester linkage within the structure thereof, or an aromatic group which contains 6 to 11 carbon atoms and may optionally be substituted, $R^3$ represents a hydrogen atom, a straight, branched or cyclic alkyl group containing 1 to 10 carbon atoms, or an aromatic group which contains 6 to 11 carbon atoms and may optionally be substituted, with a (meth) acrylic ester represented by the following formula (3):

$$CH_2=CR^1\text{-}COOR^4 \qquad (3)$$

in the formula, $R^1$ represents a hydrogen atom or a methyl group and $R^4$ represents a straight, branched or cyclic alkyl group containing 1 to 8 carbon atoms and <u>wherein said hydroxyl group-containing vinyl ether contains, as an impurity,</u> at least one compound selected from the group consisting of a divinyl ether represented by the following formula (4):

UNITED STATES PATENT AND TRADEMARK OFFICE
CERTIFICATE OF CORRECTION

| | |
|---|---|
| PATENT NO. | : 7,321,051 B2 |
| APPLICATION NO. | : 09/982861 |
| DATED | : January 22, 2008 |
| INVENTOR(S) | : Keiji Yurugi and Hiroko Yamaguchi |

It is certified that error appears in the above-identified patent and that said Letters Patent is hereby corrected as shown below:

$$R^3\text{-CH=CH-O-}R^2\text{-O-CH=CH-}R^3 \qquad (4)$$

in the formula, $R^2$ represents a straight, branched or cyclic alkylene group containing 2 to 20 carbon atoms, an alkylene group containing 2 to 20 carbon atoms and having at least one oxygen atom in the form of an ether linkage and/or an ester linkage within the structure thereof, or an aromatic group which contains 6 to 11 carbon atoms and may optionally be substituted, and the two $R^3$ groups are the same or different and each represents a hydrogen atom, a straight, branched or cyclic alkyl group containing 1 to 10 carbon atoms, or an aromatic group which contains 6 to 11 carbon atoms and may optionally be substituted, a 2-substituted-1, 3-dioxo compound represented by the following formula (5):

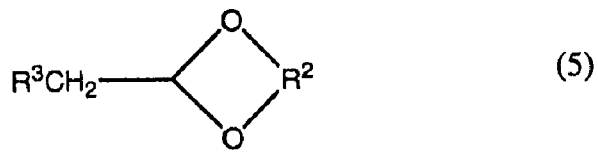

(5)

UNITED STATES PATENT AND TRADEMARK OFFICE
CERTIFICATE OF CORRECTION

| | |
|---|---|
| PATENT NO. | : 7,321,051 B2 |
| APPLICATION NO. | : 09/982861 |
| DATED | : January 22, 2008 |
| INVENTOR(S) | : Keiji Yurugi and Hiroko Yamaguchi |

It is certified that error appears in the above-identified patent and that said Letters Patent is hereby corrected as shown below:

in the formula, $R^2$ represents a straight, branched or cyclic alkylene group containing 2 to 20 carbon atoms, an alkylene group containing 2 to 20 carbon atoms and having at least one oxygen atom in the form of an ether linkage and/or an ester linkage within the structure thereof, or an aromatic group which contains 6 to 11 carbon atoms and may optionally be substituted, and $R^3$ represents a hydrogen atom, a straight, branched or cyclic alkyl group containing 1 to 10 carbon atoms, or an aromatic group which contains 6 to 11 carbon atoms, and may optionally be substituted, and an unsaturated bond-containing vinyl ether represented by the following formula (6):

$$R^3\text{-CH=CH-O-}R^5 \qquad (6)$$

in the formula, $R^3$ represents a hydrogen atom, a straight, branched or cyclic alkyl group containing 1 to 10 carbon atoms, or an aromatic group which contains 6 to 11 carbon atoms and may optionally be substituted; $R^5$ represents an organic residue containing an

UNITED STATES PATENT AND TRADEMARK OFFICE
CERTIFICATE OF CORRECTION

PATENT NO.         : 7,321,051 B2
APPLICATION NO. : 09/982861
DATED              : January 22, 2008
INVENTOR(S)        : Keiji Yurugi and Hiroko Yamaguchi It is certified that error appears in the above-identified patent and that said Letters Patent is hereby corrected as shown below:

unsaturated bond represented by $-CR^6=CR^7$; and $R^6$ and $R^7$ are the same or different and each represents a hydrogen atom or an organic residue.

Signed and Sealed this

Twenty-third Day of September, 2008

JON W. DUDAS
*Director of the United States Patent and Trademark Office*

UNITED STATES PATENT AND TRADEMARK OFFICE
CERTIFICATE OF CORRECTION

PATENT NO.        : 7,321,051 B2
APPLICATION NO.   : 09/982861
DATED             : January 22, 2008
INVENTOR(S)       : Keiji Yurugi and Hiroko Yamaguchi Page 1 of 1

It is certified that error appears in the above-identified patent and that said Letters Patent is hereby corrected as shown below:

On Title page Item [54] should read:

COMPOSITION OF VINYL ETHER GROUP-CONTAINING (METH) ACRYLIC ACID ESTER AND PRODUCTION METHOD THEREOF

Signed and Sealed this

Twenty-seventh Day of July, 2010

David J. Kappos
*Director of the United States Patent and Trademark Office*

UNITED STATES PATENT AND TRADEMARK OFFICE
CERTIFICATE OF CORRECTION

PATENT NO. : 7,321,051 B2 Page 1 of 1
APPLICATION NO. : 09/982861
DATED : January 22, 2008
INVENTOR(S) : Keiji Yurugi and Hiroko Yamaguchi It is certified that error appears in the above-identified patent and that said Letters Patent is hereby corrected as shown below:

On Title page Item [54] and at Column 1, lines 1-4, title should read:

COMPOSITION OF VINYL ETHER GROUP-CONTAINING (METH) ACRYLIC
<u>ACID</u> ESTER AND PRODUCTION METHOD THEREOF

This certificate supersedes the Certificate of Correction issued July 27, 2010.

Signed and Sealed this

Twenty-fourth Day of August, 2010

David J. Kappos
*Director of the United States Patent and Trademark Office*